United States Patent
Chang et al.

(10) Patent No.: US 7,556,867 B2
(45) Date of Patent: Jul. 7, 2009

(54) IRIDIUM (III) COMPLEX WITH HETEROATOM LINKING GROUP AND ORGANIC ELECTROLUMINESCENT DEVICE USING THE SAME

(75) Inventors: Seok Chang, Daejeon-si (KR); Hyun-Nam Cho, Gunpo-si (KR); Jong-Hyoup Lee, Seoul (KR); Lyong-Sun Pu, Suwon-si (KR); Yi-Yeol Lyu, Yongin-si (KR); Young-Hun Byun, Yongin-si (KR); Sung-Joon Kim, Yongin-si (KR); Hoon-Sik Kim, Seoul (KR)

(73) Assignee: Samsung Mobile Display Co., Ltd., Yongin, Gyunggi-Do (KR)

( * ) Notice: Subject to any disclaimer, the term of this patent is extended or adjusted under 35 U.S.C. 154(b) by 635 days.

(21) Appl. No.: 11/087,815

(22) Filed: Mar. 24, 2005

(65) Prior Publication Data
US 2005/0287391 A1 Dec. 29, 2005

(30) Foreign Application Priority Data
Jun. 29, 2004 (KR) .................. 10-2004-0049742

(51) Int. Cl.
*H01L 51/54* (2006.01)
*C09K 11/06* (2006.01)
(52) U.S. Cl. .................. 428/690; 428/917; 313/504; 313/506; 257/E51.044; 546/4; 546/5; 546/6; 546/10
(58) Field of Classification Search .................. None
See application file for complete search history.

(56) References Cited

U.S. PATENT DOCUMENTS

| | | | |
|---|---|---|---|
| 2002/0048689 A1 | 4/2002 | Igarashi et al. | |
| 2002/0064681 A1 | 5/2002 | Takiguchi et al. | |
| 2002/0182441 A1 | 12/2002 | Lamansky et al. | |
| 2003/0080342 A1* | 5/2003 | Igarashi | 257/79 |
| 2004/0053071 A1* | 3/2004 | Igarashi et al. | 428/690 |
| 2006/0163542 A1* | 7/2006 | Watanabe et al. | 252/500 |

FOREIGN PATENT DOCUMENTS

WO WO 02/15645 A1 2/2002

OTHER PUBLICATIONS

*Chinese Office Action* issued on Feb. 6, 2009 in Applicant's corresponding Chinese Patent Application No. 2005100080223 (with English translation).

* cited by examiner

*Primary Examiner*—Marie R. Yamnitzky
(74) *Attorney, Agent, or Firm*—Robert E. Bushnell, Esq.

(57) ABSTRACT

A high-efficient phosphorescent iridium (III) complex with a heteroatom linking group and an organic electroluminescent (EL) device using the same. The iridium complex is represented by Formula 1 or Formula 2:

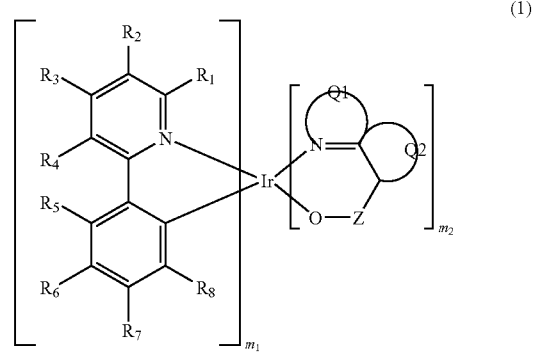

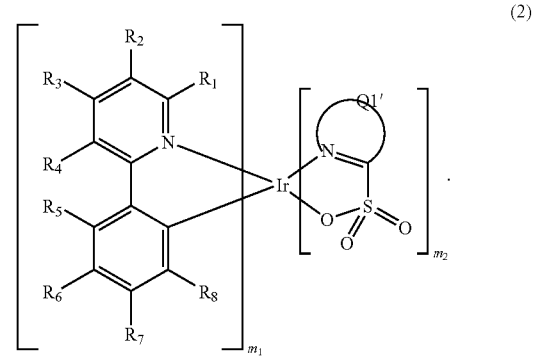

The iridium complex of the present invention complex can efficiently emit light ranging from a blue region to a red region in a triplet MLCT state. The iridium (III) complex can be used in formation of an organic layer of an organic EL device. Since the iridium complex of the present invention can be used as a high-efficiency phosphorescent material, the iridium complex of the present invention can produce white light emission when used together with a green-emitting material or a red-emitting material as well as emission at the wavelength range of 400-650 nm.

14 Claims, 5 Drawing Sheets

US 7,556,867 B2

IRIDIUM (III) COMPLEX WITH HETEROATOM LINKING GROUP AND ORGANIC ELECTROLUMINESCENT DEVICE USING THE SAME

CLAIM OF PRIORITY

This application claims priority from Korean Patent Application No. 10-2004-0049742, filed on Jun. 29, 2004, in the Korean Intellectual Property Office, the disclosure of which is incorporated herein in its entirety by reference.

BACKGROUND OF THE INVENTION

1. Field of the Invention

The present invention relates to an iridium (III) complex with a heteroatom linking group and an organic electroluminescent device using the same. More particularly, the present invention relates to an iridium (III) complex that can emit light ranging from a blue region to a red region in a triplet metal-to-ligand charge-transfer (MLCT) state and an organic electroluminescent device using the iridium (III) complex as an organic layer material.

2. Description of the Related Art

Organic electroluminescent (EL) devices are self-emission displays that emit light by recombination of electrons and holes in a thin layer (hereinafter, referred to as "organic layer") made of a fluorescent or phosphorescent organic compound when a current is applied to the organic layer. The organic EL devices have advantages such as lightweight, simple constitutional elements, easy fabrication process, superior image quality, and wide viewing angle. In addition, the organic EL devices have electrical properties suitable for portable electronic equipment such as high color purity, perfect creation of dynamic images, low power consumption, and low driving voltage.

A common organic EL device has a sequentially stacked structure of an anode, a hole transport layer, a light emission layer, an electron transport layer, and a cathode, on an upper surface of a substrate. The hole transport layer, the light emission layer, and the electron transport layer are organic layers made of an organic compound. The organic EL device with the above-described structural feature is driven as follows. When a voltage is applied to the anode and the cathode, holes from the anode are transferred to the light emission layer via the hole transport layer. On the other hand, electrons from the cathode are transferred to the light emission layer via the electron transport layer. Carriers recombine at the light emission layer to generate excitons. By the radiative decay of the excitons, light emission occurs at the wavelength corresponding to the band gap of a material.

The material for the light emission layer in the organic EL device is divided into a fluorescent material using a singlet exciton and a phosphorescent material using a triplet exciton according to emission mechanism. The light emission layer is formed of the fluorescent or phosphorescent material alone or an appropriate host material doped with the fluorescent or phosphorescent material. Singlet excitons and triplet excitons are formed in the host during electronic excitation. At this time, a statistical ratio of the singlet excitons to the triplet excitons is 1 to 3.

An organic EL device including a light emission layer made of a fluorescent material has a disadvantage in that triplet excitons formed in a host are wasted. On the other hand, an organic EL device including a light emission layer made of a phosphorescent material has an advantage of 100% internal quantum efficiency since both singlet excitons and triplet excitons can be utilized. In this respect, a light emission layer made of a phosphorescent material can achieve significantly high emission efficiency, relative to a light emission layer made of a fluorescent material.

When a heavy metal such as Ir, Pt, Rh, and Pd is introduced into an organic molecule, the heavy atom effect leads to spin-orbital coupling, whereby a triplet state and a singlet state are mixed. Therefore, a forbidden transition is induced, which allows efficient phosphorescent emission even at room temperature.

Recently, there has been developed high-efficiency, green and red phosphorescent materials with 100% internal quantum efficiency.

As a high-efficiency phosphorescent material, there have been reported various materials based on transition metal compounds containing transition metals such as iridium and platinum. To date, green and red phosphorescent materials satisfying characteristics required for high-efficiency full-color displays or white electroluminescence with low power consumption have existed. However, efficient and reliable blue phosphorescent materials have not been developed, which is a significant obstruction to the development of phosphorescent full-color devices.

In view of this problem, a blue-emitting material has been developed (WO 02/15645 A1, US 2002/0064681 A1 entitled Luminescence device, display apparatus and metal coordination compound to Takiguchi et al., and published on May 30, 2002). Furthermore, there has been developed an organometallic complex having a bulky functional group capable of increasing a HOMO (Highest Occupied Molecular Orbital: HOMO)-LUMO (Lowest Unoccupied Molecular Orbital: LUMO) energy gap by a geometrical change or a functional group (e.g., cyano group) with high ligand field strength. In addition, there have been developed an iridium complex represented by formula $Ir(ppy)_2P(ph)_3Y$ (Y=Cl or CN) (US2002/0182441 A1 entitled Organometallic compounds and emission-shifting organic electrophosphorescence to Lamansky et al. and published on Dec. 5, 2002) and an iridium (III) complex having a cyclometallated ligand, a chelating diphosphine, chlorine, and cyano group (US 2002/0048689 A1 entitled Light-emitting device and iridium complex to Igarashi et al. and published on Apr. 25, 2002).

SUMMARY OF THE INVENTION

It is therefore an object of the present invention to provide a novel compound for an organic electroluminescent (EL) device.

It is also an object of the present invention to provide an improved organic electroluminescent (EL) device.

It is further an object of the present invention to provide an iridium (III) complex with a heteroatom linking group that can efficiently emit light ranging from a blue region to a red region in a triplet metal-to-ligand charge-transfer (MLCT) state.

It is still an object of the present invention to provide an organic electroluminescent (EL) device that can efficiently emit light ranging from a blue region to a red region.

The above and other objects can be achieved by the present invention.

According to an aspect of the present invention, there is provided an iridium (III) complex represented by Formula 1:

[Formula 1]

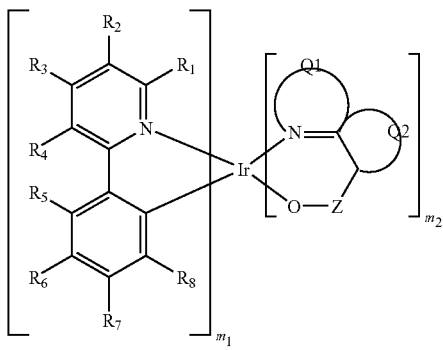

wherein Q1 is an N-containing aromatic ring and Q2 is an aromatic ring fused to Q1;

Z is a carbonyl linking group (>C═O), an alkylene group, an oxygen atom linking group (—O—), a nitrogen atom linking group (—NH—), a thiocarbonyl linking group (>C═S), a sulfoxide linking group (>S═O), a sulfonyl linking group (—SO$_2$—), or a combination thereof;

$m_1$ is an integer of 0 to 2 and $m_2$ is 3−$m_1$; and $R_1$, $R_2$, $R_3$, $R_4$, $R_5$, $R_6$, $R_7$, and $R_8$ are each independently a hydrogen or a substituent.

According to another aspect of the present invention, there is provided an iridium (III) complex represented by Formula 2:

[Formula 2]

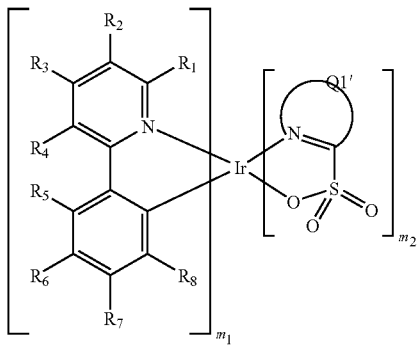

wherein Q1' is an N-containing aromatic ring;

$m_1$ is an integer of 0 to 2 and $m_2$ is 3−$m_1$; and $R_1$, $R_2$, $R_3$, $R_4$, $R_5$, $R_6$, $R_7$, and $R_8$ are each a hydrogen or a substituent.

According to still another aspect of the present invention, there is provided an organic EL device including an organic layer interposed between a pair of electrodes, wherein the organic layer includes the iridium (III) complex of the above formula 1.

According to yet another aspect of the present invention, there is provided an organic EL device including an organic layer interposed between a pair of electrodes, wherein the organic layer includes the iridium (III) complex of the above formula 2.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE PREFERRED EMBODIMENTS

Figure 1:
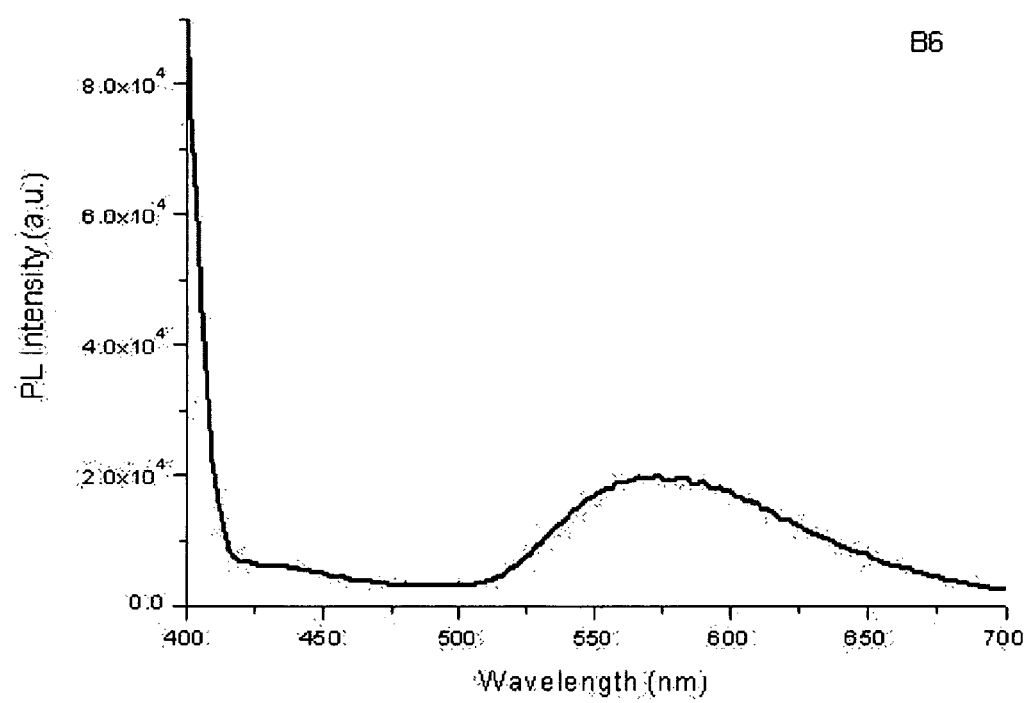
FIG. 1 is a photoluminescent (PL) spectrum of a compound of Example 1 of the present invention.

Hereinafter, the preferred embodiments of the present invention will be described in more detail.

An iridium complex according to the present invention can increase the energy gaps of highest occupied molecular orbital (HOMO) and triplet metal-to-ligand charge-transfer (MLCT) states, which enables blue light emission. The increase of the energy gaps of the HOMO and triplet MLCT states can be induced by coordinating a bulky ligand to distort the structure of the molecule, and by the introduction of a ligand capable of providing a strong ligand field exhibiting excellent σ-donor or π-donor capability.

An iridium complex with a heteroatom linking group of the present invention is represented by the following formula 1:

[Formula 1]

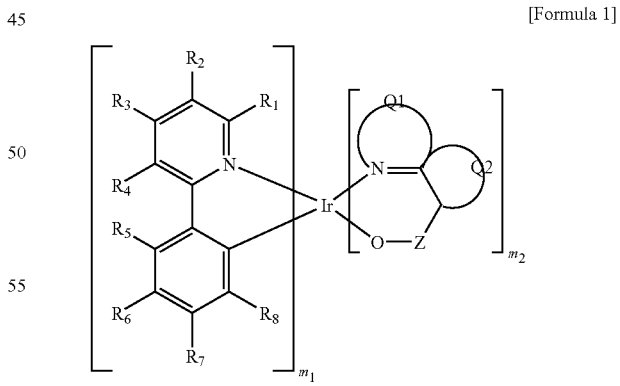

wherein Q1 is an N-containing aromatic ring and Q2 is an aromatic ring fused to Q1;

Z is a carbonyl linking group (>C═), an alkylene group, an oxygen atom linking group (—O—), a nitrogen atom linking group (—NH—), a thiocarbonyl linking group (>C═S), a sulfoxide linking group (>S═O), a sulfonyl linking group (—SO$_2$—), or a combination thereof;

$m_1$ is an integer of 0 to 2 and $m_2$ is $3-m_1$; and $R_1$, $R_2$, $R_3$, $R_4$, $R_5$, $R_6$, $R_7$, and $R_8$ are each a hydrogen or a substituent.

The iridium complex of the above formula 1 is characterized in that the substituents Q1 and Q2 form a fused ring.

Preferably, Q1 is a N-containing hetero-aromatic ring of 4-30 carbon atoms and Q2 is an aromatic ring of 5-30 carbon atoms.

For example, a fused ring formed by Q1 and Q2 is derived from one selected from the group consisting of indole, azaindole, carbazole, indazole, harmane, benzimidazole, benzotriazole, benzoxazole, benzothiazole, benzoselenadiazole, benzothiadiazole, benzisoxazole, quinoline, benzoquinoline, acridine, isoquinoline, and a derivative thereof.

$R_1$, $R_2$, $R_3$, $R_4$, $R_5$, $R_6$, $R_7$, and $R_8$ are each independently a substituent selected from the group consisting of an alkyl group (preferably having 1-30 carbon atoms, more preferably 1-20 carbon atoms, and still more preferably 1-10 carbon atoms), an alkenyl group (preferably having 2-30 carbon atoms, more preferably 2-20 carbon atoms, and still more preferably 2-10 carbon atoms), an alkynyl group (preferably having 2-30 carbon atoms, more preferably 2-20 carbon atoms, and still more preferably 2-10 carbon atoms), an aryl group (preferably 6-30 carbon atoms, more preferably 6-20 carbon atoms, and still more preferably 6-12 carbon atoms), an amino group (preferably having 0-30 carbon atoms, more preferably 0-20 carbon atoms, and still more preferably 0-10 carbon atoms), an alkoxy group (preferably having 1-30 carbon atoms, more preferably 1-20 carbon atoms, and still more preferably 1-10 carbon atoms), an aryloxy group (preferably having 6-30 carbon atoms, more preferably 6-20 carbon atoms, and still more preferably 6-12 carbon atoms), a heterocyclic oxy group (preferably having 1-30 carbon atoms, more preferably 1-20 carbon atoms, and still more preferably 1-12 carbon atoms), an acyl group (preferably having 1-30 carbon atoms, more preferably 1-20 carbon atoms, and still more preferably 1-12 carbon atoms), an alkoxycarbonyl group (preferably having 2-30 carbon atoms, more preferably 2-20 carbon atoms, and still more preferably 2-12 carbon atoms), an aryloxycarbonyl group (preferably having 7-30 carbon atoms, more preferably 7-20 carbon atoms, and still more preferably 7-12 carbon atoms), an acyloxy group (preferably 2-30 carbon atoms, more preferably 2-20 carbon atoms, and still more preferably 2-10 carbon atoms), an acylamino group (preferably 2-30 carbon atoms, more preferably 2-20 carbon atoms, and still more preferably 2-10 carbon atoms), an alkoxycarbonylamino group (preferably having 2-30 carbon atoms, more preferably 2-20 carbon atoms, and still more preferably 2-12 carbon atoms), an aryloxycarbonylamino group (preferably having 7-30 carbon atoms, more preferably 7-20 carbon atoms, and still more preferably 7-12 carbon atoms), a sulfonylamino group (preferably 1-30 carbon atoms, more preferably 1-20 carbon atoms, and still more preferably 1-12 carbon atoms), a sulfamoyl group (preferably having 0-30 carbon atoms, more preferably 0-20 carbon atoms, and still more preferably 0-12 carbon atoms), a carbamoyl group (preferably having 1-30 carbon atoms, more preferably 1-20 carbon atoms, and still more preferably 1-12 carbon atoms), an alkylthio group (preferably having 1-30 carbon atoms, more preferably 1-20 carbon atoms, and still more preferably 1-12 carbon atoms), an arylthio group (preferably having 6-30 carbon atoms, more preferably 6-20 carbon atoms, and still more preferably 6-12 carbon atoms), a heterocyclic thio group (preferably having 1-30 carbon atoms, more preferably 1-20 carbon atoms, and still more preferably 1-12 carbon atoms), a sulfonyl group (preferably having 1-30 carbon atoms, more preferably 1-20 carbon atoms, and still more preferably 1-12 carbon atoms), a sulfinyl group (preferably having 1-30 carbon atoms, more preferably 1-20 carbon atoms, and still more preferably 1-12 carbon atoms), an ureido group (preferably having 1-30 carbon atoms, more preferably 1-20 carbon atoms, and still more preferably 1-12 carbon atoms), a phosphoramide group (preferably 1-30 carbon atoms, more preferably 1-20 carbon atoms, and still more preferably 1-12 carbon atoms), a hydroxyl group, a mercapto group, a halogen atom, a cyano group, a sulfo group, a carboxyl group, a nitro group, a hydroxaminic group, a sulfino group, a hydrazino group, an imino group, a heterocyclic group (preferably having 1-30 carbon atoms, more preferably 1-12 carbon atoms), a silyl group (preferably having 3-40 carbon atoms, more preferably 3-30 carbon atoms, and still more preferably 3-24 carbon atoms), and a silyloxy group (preferably having 3-40 carbon atoms, more preferably 3-30 carbon atoms, and still more preferably 3-24 carbon atoms).

In particular, the iridium complex of the above formula 1 may be one selected from compounds represented by the following formulae 3 and 4, but is not limited thereto:

[Formula 3]

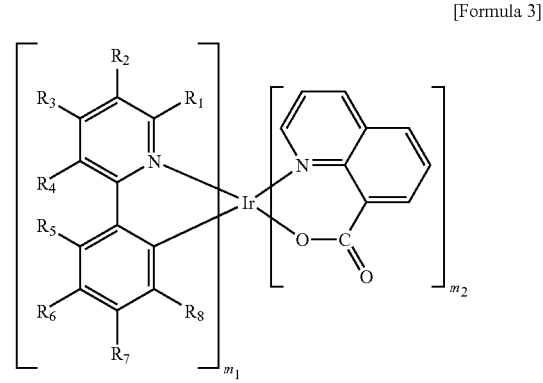

[Formula 4]

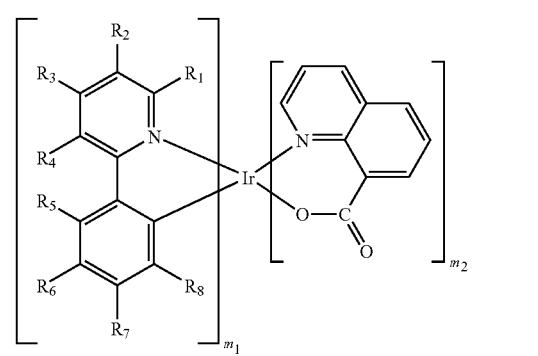

wherein $R_1$, $R_2$, $R_3$, $R_4$, $R_5$, $R_6$, $R_7$, $R_8$, $m_1$, and $m_2$ are as defined in the above formula 1.

More illustrative examples of the iridium complex of the above formula 1 include compounds represented by the following formulae:
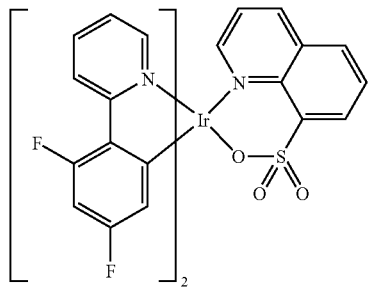
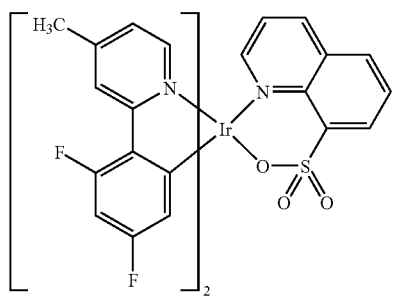
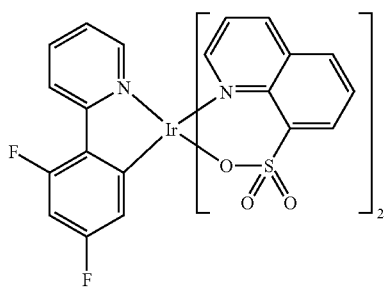
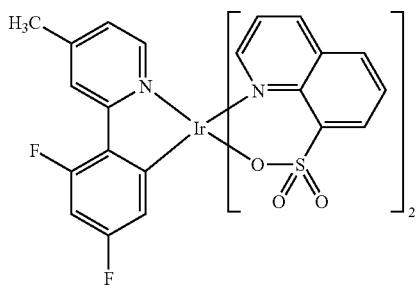
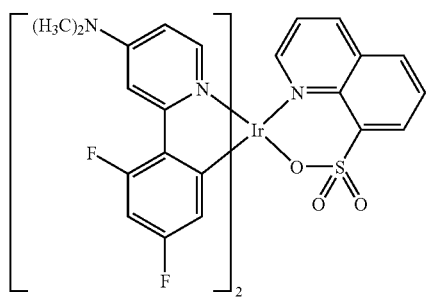
-continued
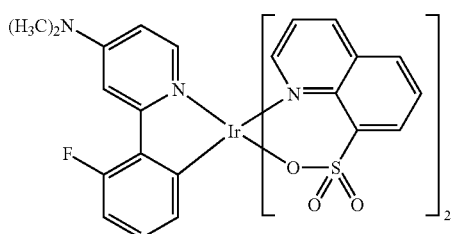
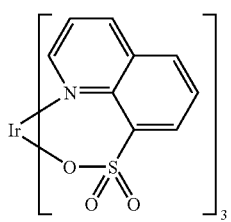
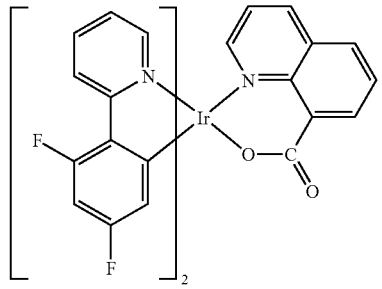
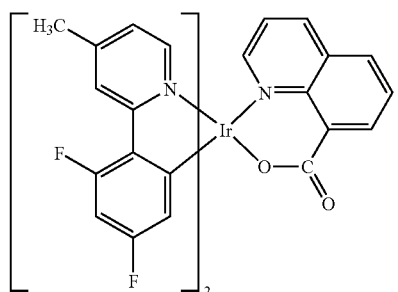
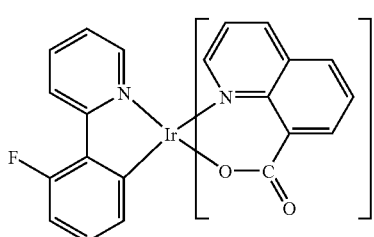
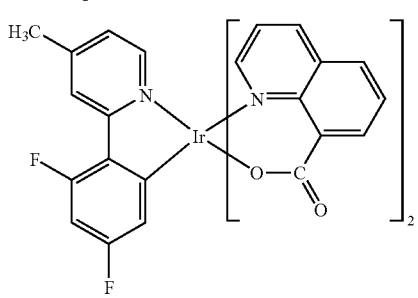

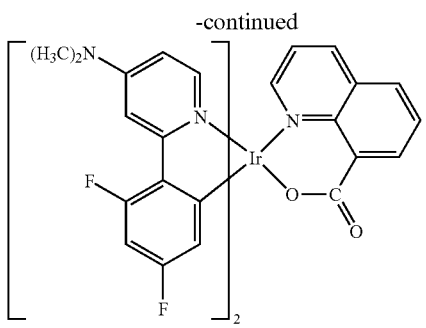
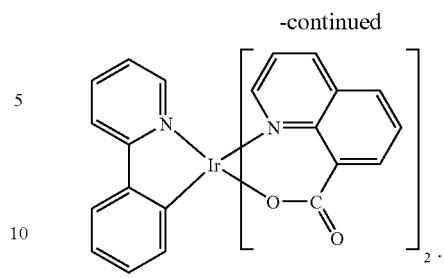

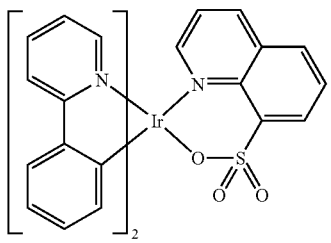

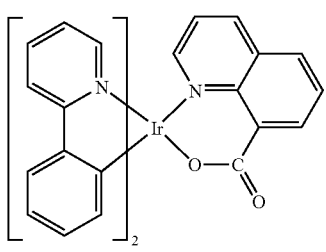

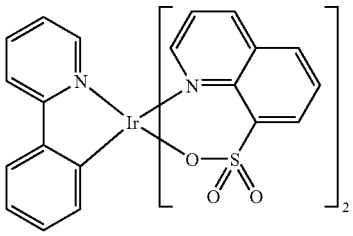

An iridium complex with a heteroatom linking group according to the present invention is also represented by the following formula 2:

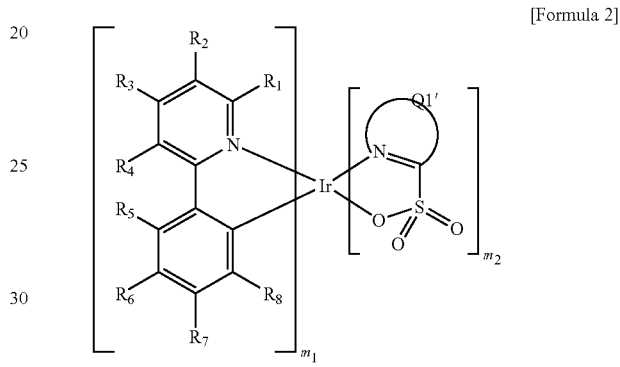

[Formula 2]

wherein Q1' is an N-containing aromatic ring;

$m_1$ is an integer of 0 to 2 and $m_2$ is $3-m_1$; and $R_1$, $R_2$, $R_3$, $R_4$, $R_5$, $R_6$, $R_7$, and $R_8$ are each a hydrogen or a substituent.

Preferably, Q1' is an N-containing aromatic ring of 4-20 carbon atoms.

For example, Q1' is derived from one selected from the group consisting of pyrimidine, indole, azaindole, carbazole, indazole, harmane, pyrazole, pyrrole, benzimidazole, benzotriazole, benzoxazole, benzothiazole, benzoselenadiazole, benzothiadiazole, isoxazole, isothiazole, thiadiazole, triazine, benzisoxazole, pyrazine, quinoline, benzoquinoline, acridine, isoquinoline, and a derivative thereof.

In the above formula 2, illustrative examples of $R_1$, $R_2$, $R_3$, $R_4$, $R_5$, $R_6$, $R_7$, and $R_8$ are as defined in the above formula 1.

Illustrative examples of the iridium complex of the above formula 2 include compounds represented by the following formulae:

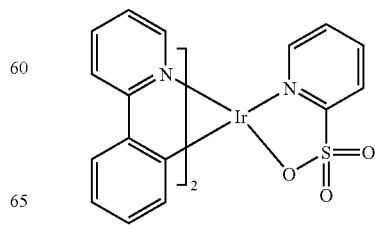

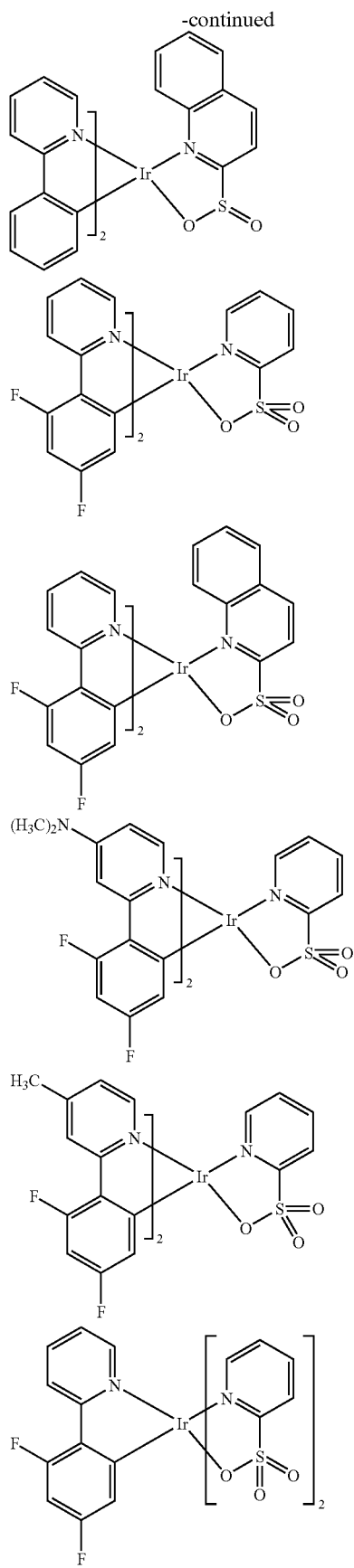
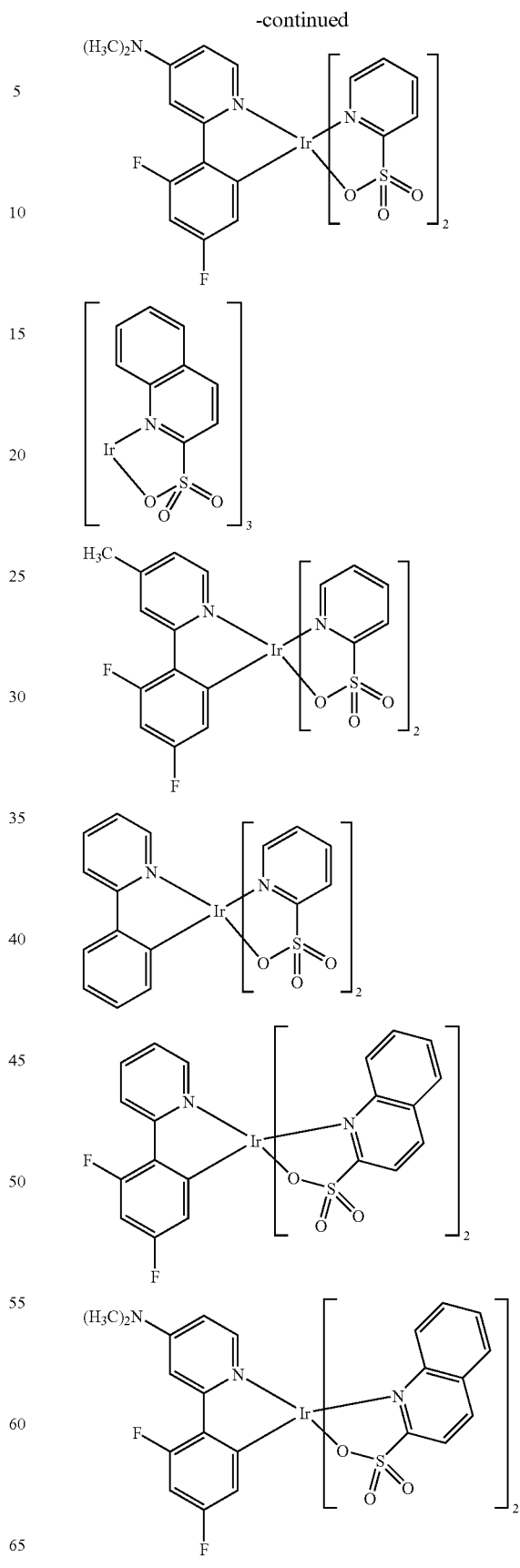

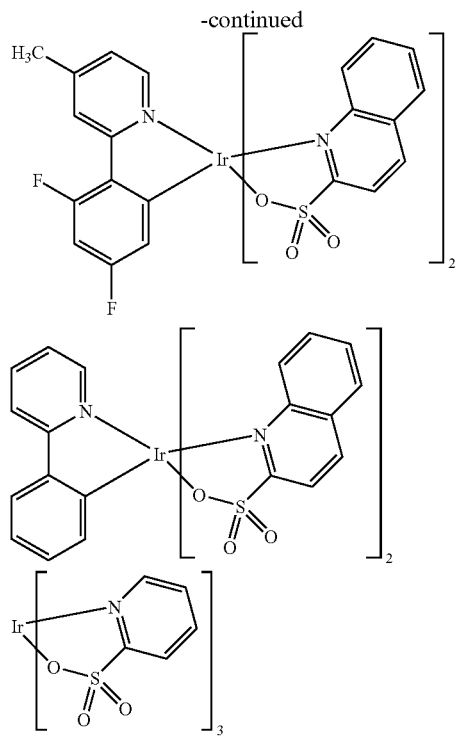

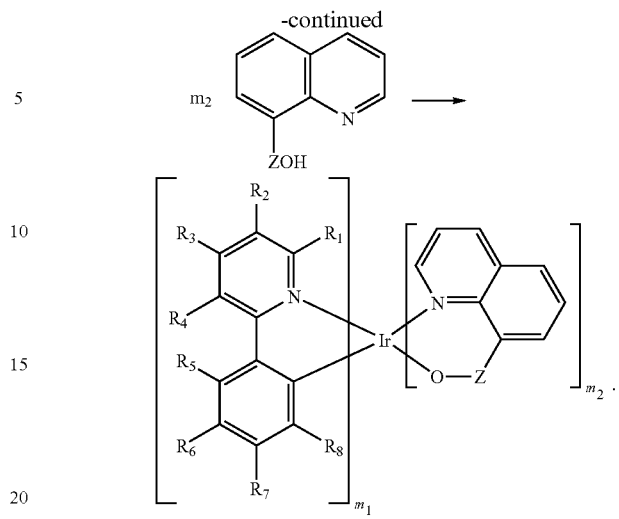

In the above reaction scheme 1, the cyclometallated ligand and the N-containing aromatic compound are as defined in the above.

The iridium complex of formula 2 according to the present invention can be synthesized in a similar manner to the reaction scheme 1. That is, the iridium complex of formula 2 can be synthesized by varying the type of the N-containing aromatic compound.

An organic EL device of the present invention is manufactured by forming an organic layer, in particular a light emission layer, using an iridium complex of the present invention. At this time, the iridium complexes of the above formulae 1 and 2 are effectively used as phosphorescent dopants which are light emission layer materials and exhibit excellent emission characteristics at a blue wavelength region.

When an iridium complex according to the present invention is used as a phosphorescent dopant, the organic layer may further include one or more selected from the group consisting of at least one polymeric host, a mixture of a polymeric host and a small molecular host, a small molecular host, and a non-emission polymeric matrix. There are no limitations on the polymeric host, the small molecular host, and the non-emission polymeric matrix provided that they are those as used commonly in formation of light emission layers for organic EL devices. Examples of the polymeric host include polyvinylcarbazole (PVK) and polyfluorene, examples of the small molecular host include CBP (4,4'-N,N'-dicarbazole-biphenyl), 4,4'-bis[9-(3,6-biphenylcarbazolyl)]-1,1'-biphenyl, 9,10-bis[(2',7'-t-butyl)-9',9"-spirobifluorenylanthracene, and tetrafluorene, and examples of the non-emission polymeric matrix include polymethylmethacrylate and polystyrene, but are not limited thereto.

Preferably, an iridium complex according to the present invention is used in an amount of 1 to 30 parts by weight, based on 100 parts by weight of the total weight of a light emission layer material. The iridium complex can be incorporated in the light emission layer by vacuum deposition, sputtering, printing, coating, ink-jet, or e-beam.

An iridium complex according to the present invention can produce white light emission when used together with a green-emitting material or a red-emitting material.

Preferably, the thickness of the organic layer ranges from 30 to 100 nm. As used herein, the organic layer is a layer made of an organic compound interposed between a pair of electrodes in an organic EL device, for example an electron trans- An iridium complex according to the present invention has emission characteristics at the wavelength range of 400 to 650 nm.

An iridium complex according to the present invention can be synthesized by applying the method reported by Watts group [F. O. Garces, R. J. Watts, Inorg. Chem. 1988, (35), 2450, which is incorporated herein by reference.] using [Ir(C^N)$_2$Cl]$_2$ derivative which is a starting material serving as a cyclometallated moiety donor.

Hereinafter, synthetic pathways of iridium complexes according to embodiments of the present invention will be described.

Referring to the following reaction scheme 1, a [Ir(C^N)$_{m1}$(N^O)$_{m2}$] compound according to the present invention can be synthesized by mixing a [Ir(C^N)$_2$Cl]$_2$ derivative and an N-containing aromatic compound which are starting materials with a solvent such as 1,2-dichloromethane, methylenechloride, and tetrahydrofuran (THF) followed by stirring at room temperature for 2-48 hours:

[Reaction Scheme 1]

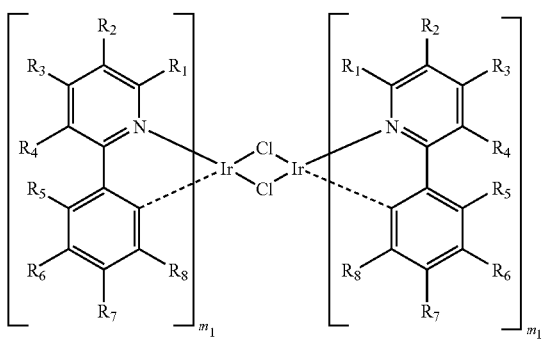

port layer and a hole transport layer, in addition to a light emission layer. Such an organic EL device can have such a structure as anode/light emission layer/cathode, anode/buffer layer/light emission layer/cathode, anode/hole transport layer/light emission layer/cathode, anode/buffer layer/hole transport layer/light emission layer/cathode, anode/buffer layer/hole transport layer/light emission layer/electron transport layer/cathode, anode/buffer layer/hole transport layer/light emission layer/hole blocking layer/cathode, as commonly known in the art, but is not limited thereto.

The buffer layer may be made of a material commonly used in the art, preferably, copper phthalocyanine, polythiophene, polyaniline, polyacetylene, polypyrrole, polyphenylenevinylene, or a derivative thereof, but is not limited thereto.

The hole transport layer may be made of a material commonly used in the art, preferably polytriphenylamine, but is not limited thereto.

The electron transport layer may be made of a material commonly used in the art, preferably polyoxadiazole, but is not limited thereto.

The hole blocking layer may be made of a material commonly used in the art, preferably LiF, $BaF_2$, or $MgF_2$, but is not limited thereto.

An organic EL device according to the present invention can be manufactured by a common organic EL device manufacturing method using a common light-emitting material without requiring a particular apparatus.

An iridium complex according to the present invention can produce light emission at the wavelength range of 400 to 650 nm. A light emission diode using such an organometallic complex can be used in optical illumination sources for full-color displays, backlighting, exterior bulletin boards, optical communication, interior decoration, and the like.

Hereinafter, the present invention will be described more specifically by Examples. However, the following Examples are provided only for illustrations and thus the present invention is not limited to or by them.

REFERENCE EXAMPLE 1

Synthesis of $F_2$ppy Dimer

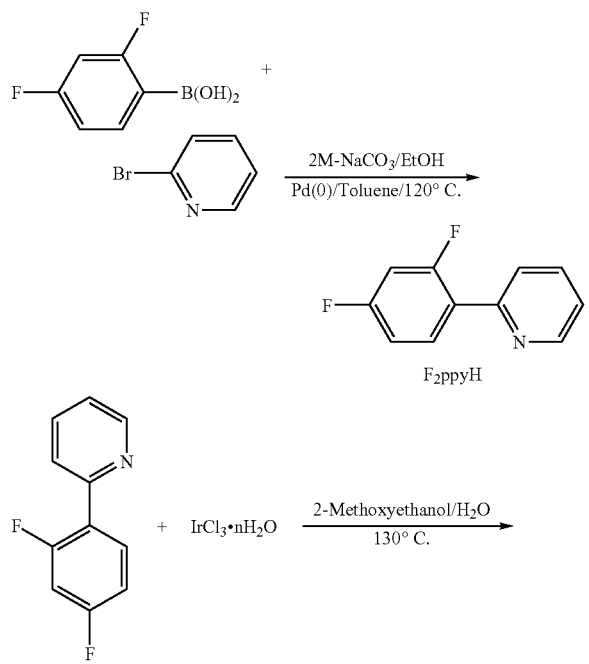

19.85 g ($1.25\times10^4$ mmol) of 2-bromopyridine, 25.00 g ($1.58\times10^4$ mmol) of 2,4-2,4-difluorophenylboronic acid, 100 mL of toluene, and a 2M sodium carbonate solution prepared from 48 mL of ethanol and 95 mL of water were added to a 500 mL side-armed flask and stirred at room temperature under a nitrogen atmosphere. Then, 4.53 g (3.92 mmol) of tetrakis(triphenylphosphine)palladium (0) was added to the reaction mixture and refluxed for 15 hours in the dark under a nitrogen atmosphere.

After the reaction terminated, the reaction mixture was set to room temperature followed by extraction with ethylacetate and water and then separation by column chromatography (toluene:hexane=10:1) to obtain a light brown liquid ($F_2$ppyH).

$^1$H-NMR($CD_2Cl_2$, ppm): 8.69(d, 1H), 8.03(m, 1H), 7.70 (m, 2H), 7.27(m, 1H), 7.00(m, 2H)

$F_2$ppy dimer of a yellow powder was synthesized from the 2-(4,6-difluorophenylpyridine)monomer as synthesized according to the above procedure and $IrCl_3 \cdot nH_2O$. At this time, reference was made to a synthesis method disclosed in J. Am. Che. Soc., 1984, 106, 6647-6653, which is incorporated herein by reference.

$^1$H-NMR($CD_2Cl_2$, ppm): 9.1(d, 4H), 8.3(d, 4H), 7.9(t, 4H), 6.9(m, 4H), 6.5(m, 4H), 5.3(d, 4H)

REFERENCE EXAMPLE 2

Synthesis of $F_2$pmp Dimer

F$_2$pmp dimer was synthesized in the same manner as in Reference Example 1 except that 2-bromo-4-methylpyridine was used instead of 2-bromopyridine.

$^1$H-NMR(CD$_2$Cl$_2$, ppm): 8.9(d, 4H), 8.1(s, 4H), 6.6(d, 4H), 6.3(m, 4H), 5.3(d, 4H), 2.6(s, 12H)

REFERENCE EXAMPLE 3

Synthesis of DMAF$_2$ppy Dimer

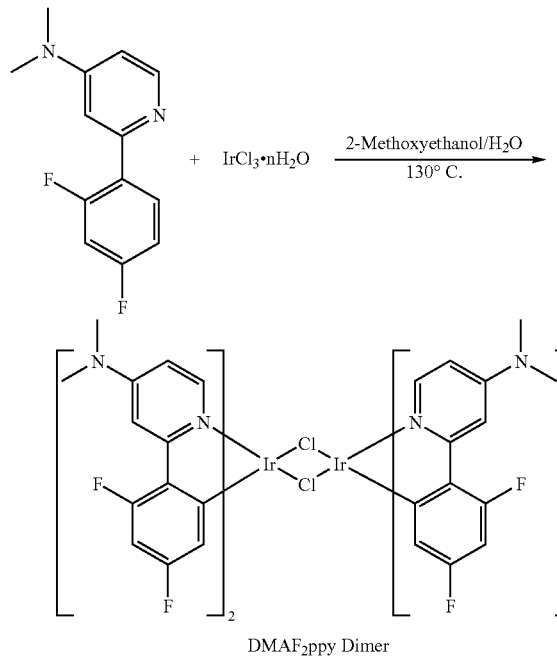

DMAF$_2$ppy Dimer

DMAF$_2$ppy dimer was synthesized in the same manner as in Reference Example 1 except that 25.26 g (1.25×10$^4$ mmol) of 2-bromo-4-dimethylaminopyridine was used instead of 2-bromopyridine.

$^1$H-NMR(CD$_2$Cl$_2$, ppm): 8.7(d, 4H), 7.5(t, 4H), 6.3(m, 4H), 6.1(m, 4H) 5.4(d, 4H), 3.2(s, 24H)

REFERENCE EXAMPLE 4

Synthesis of ppy Dimer

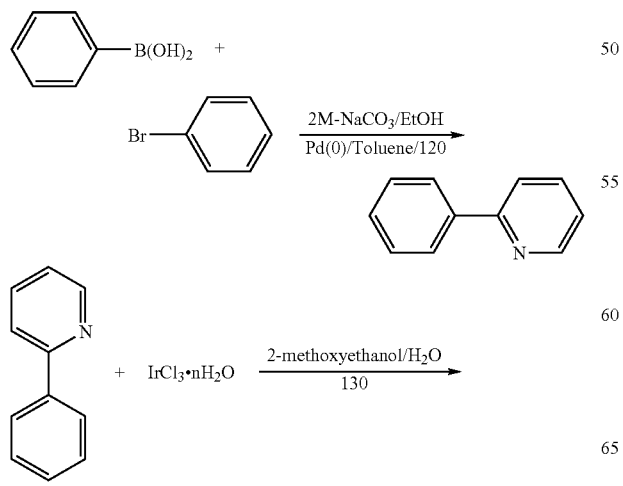

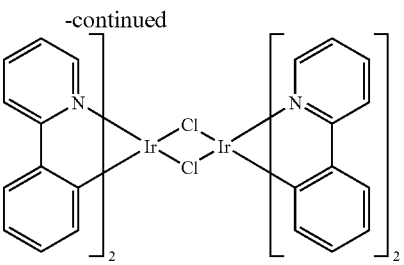

ppy dimer was synthesized in the same manner as in Reference Example 1 except that 19.30 g (1.58×10$^4$ mmol) of phenylboronic acid was used instead of 2,4-difluorophenylboronic acid.

The EL spectra of compounds synthesized in the following Examples were obtained by using multilayer EL devices which had the following structure and an emission area of 9 mm$^2$:

substrate/first electrode/hole injection layer/hole transport layer/light emission layer/hole blocking layer/electron transport layer/electron injection layer/second electrode (glass/ITO/m-MTDATA(60 nm)/NBP(15 nm)/CBP+Dopant(7%) (30 nm)/BCP(10 nm)/Alq3(20 nm)/LiF(2 nm)/Al(200 nm)).

EXAMPLE 1

Synthesis of iridium (III) bis(2-(4',6'-difluorophenyl) pyridinato-N,C$^{2'}$)8-quinolinecarboxylate (B6)

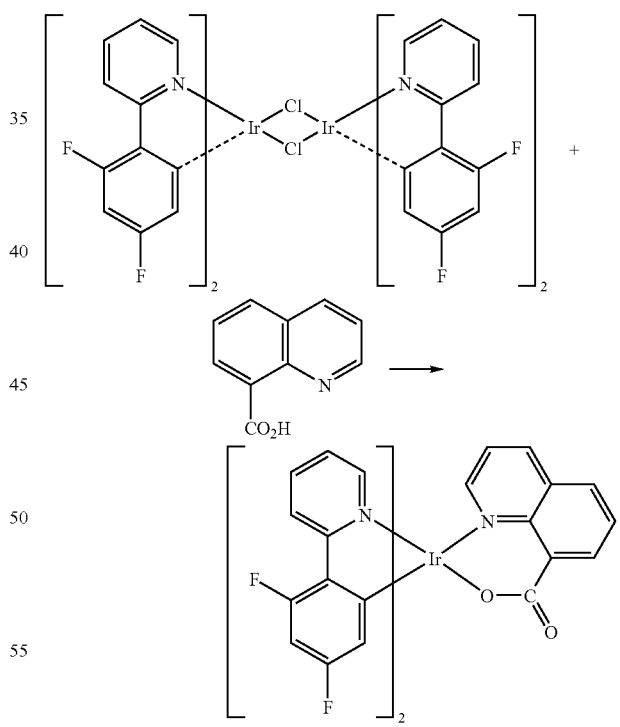

1 g (0.82 mmol) of [(F$_2$ppy)$_2$IrCl]$_2$ synthesized in Reference Example 1 and 0.36 g (2.06 mmol) of 8-quinolinecarboxylic acid were dissolved in 60 ml of 2-ethoxyethanol in a 100 ml two-neck flask equipped with a thermocouple, a mechanical stirrer, and a reflux condenser under a nitrogen atmosphere. 0.5 g of sodium carbonate (Na$_2$CO$_3$) was added thereto, stirred at room temperature for two hours, and refluxed for 8 hours with gradually increasing a reaction temperature. After the reaction terminated, the reaction solution was cooled to room temperature and an undissolved starting material remained unreacted was removed by filtration. A solvent used was completely removed from a filtrate using a rotary evaporator followed by dropwise addition of diethylether. A yellow solid formed at this time was filtered with a filter paper and then several times washed with diethylether and hexane. The resultant yellow solid was sufficiently dried at a 30° C. vacuum oven to give 1.15 g (yield 93.90%) of the title compound as a pure yellow solid. The melting point was 341-343° C. $^1$H-NMR(CDCl$_3$): δ 5.48(d, 1H, aromatic), 5.68(d, 1H, aromatic), 6.41(m, 1H, aromatic), 6.77(t, 1H, aromatic), 7.15-7.23(m, 2H, aromatic), 7.40(d, 1H, aromatic), 7.69-7.85(m, 1H, aromatic), 7.98(d, 1H, aromatic), 8.28(d, 2H, aromatic), 9.10(d, 1H, aromatic).

Emission characteristics of the compound obtained according to the above procedure were evaluated by the following methods.

A first method is to evaluate the emission characteristics of $10^{-4}$ M methylenechloride solution prepared by dissolving the compound in methylenechloride. A second method is to evaluate the emission characteristics of a film formed by dissolving 94 parts by weight of polymethylmethacrylate (PMMA) and 6 parts by weight of the compound in a solvent followed by spin-coating.

According to the evaluation results of the emission characteristics, the compound in a liquid state exhibited the maximum emission intensity at the wavelength of about 575 nm, as shown in the PL spectrum of FIG. 1.

EXAMPLE 2

Synthesis of iridium (III) bis(2-(4',6'-difluorophenyl)pyridinato-N,C$^{2'}$)8-quinolinesulfonate (B5)

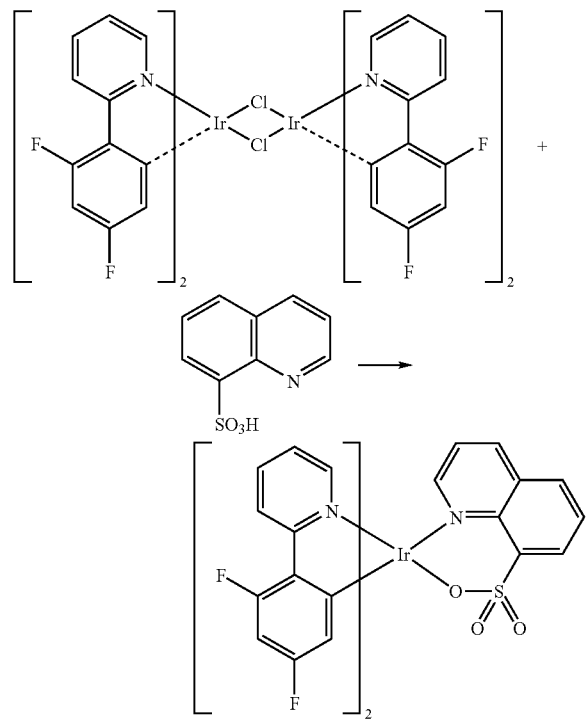

1.19 g (yield 92.68%) of the title compound was synthesized as a pure yellow solid in the same manner as in Example 1 except that 0.43 g (2.06 mmol) of 8-quinolinesulfonic acid was used instead of 0.36 g of 8-quinolinecarboxylic acid. The melting point was 395° C. or more. $^1$H-NMR(CDCl$_3$): δ 5.67(d, 1H, aromatic), 5.76(d, 1H, aromatic), 5.42(m, 1H, aromatic), 6.90(d, 1H, aromatic), 7.68(t, 1H, aromatic), 7.88 (d, 1H, aromatic), 8.20(d, 1H, aromatic), 8.32(d, 1H, aromatic), 8.67(d, 1H, aromatic), 8.77(d, 1H, aromatic), 8.82(d, 1H, aromatic), 8.98(d, 1H, aromatic).

Figure 2:
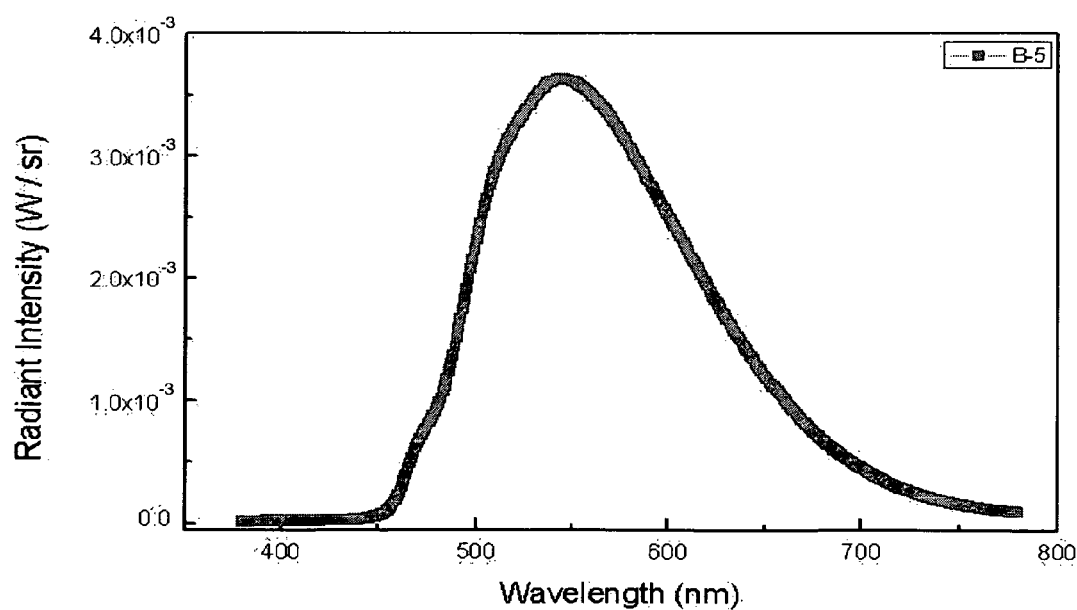
FIG. 2 is an electroluminescent (EL) spectrum of a compound of Example 2 of the present invention.

The compound in a liquid state exhibited the maximum emission intensity at the wavelength of 546 nm, as shown in the EL spectrum of FIG. 2.

The CIE chromaticity coordinate of the compound showed that x was 0.396 and y was 0.529.

EXAMPLE 3

Synthesis of iridium (III) bis(2-phenylpyridinato-N, C$^{2'}$)8-quinolinecarboxylate (A6)

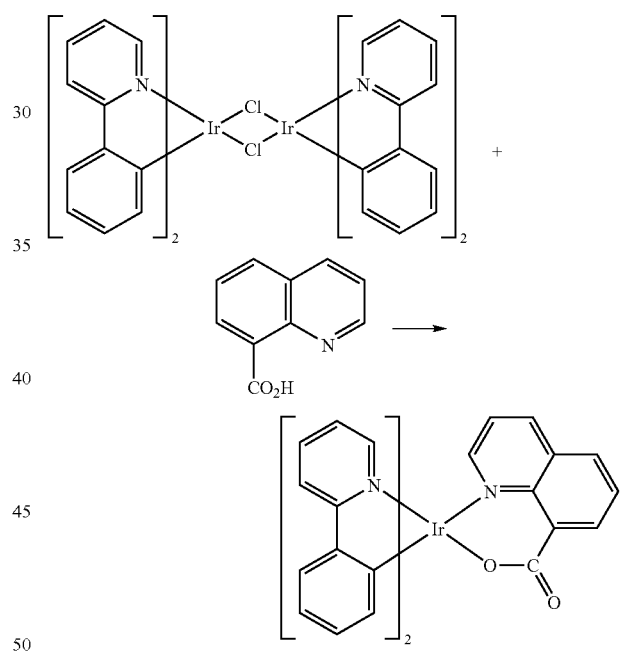

0.89 g (yield 70.97%) of the title compound was synthesized as a pure yellow solid in the same manner as in Example 1 except that 1 g (0.93 mmol) of [(ppy)$_2$IrCl]$_2$ synthesized in Reference Example 4 was used instead of 1 g (0.82 mmol) of [(F$_2$ppy)$_2$IrCl]$_2$. The melting point was 351-353° C. $^1$H-NMR(CDCl$_3$): δ 6.08 (d, 1H, aromatic), 6.25 (d, 1H, aromatic), 6.72 (q, 1H, aromatic), 6.83 (t, 1H, aromatic), 6.90 (t, 1H, aromatic), 7.11 (d, 1H, aromatic), 7.42 (d, 1H, aromatic), 7.53 (d, 1H, aromatic), 7.63-7.74 (m, 1H, aromatic), 7.85-7.96 (m, 1H, aromatic), 8.24 (d, 1H, aromatic), 8.33 (d, 1H, aromatic), 9.07 (d, 1H, aromatic), 9.14 (d, 1H, aromatic).

Figure 3:
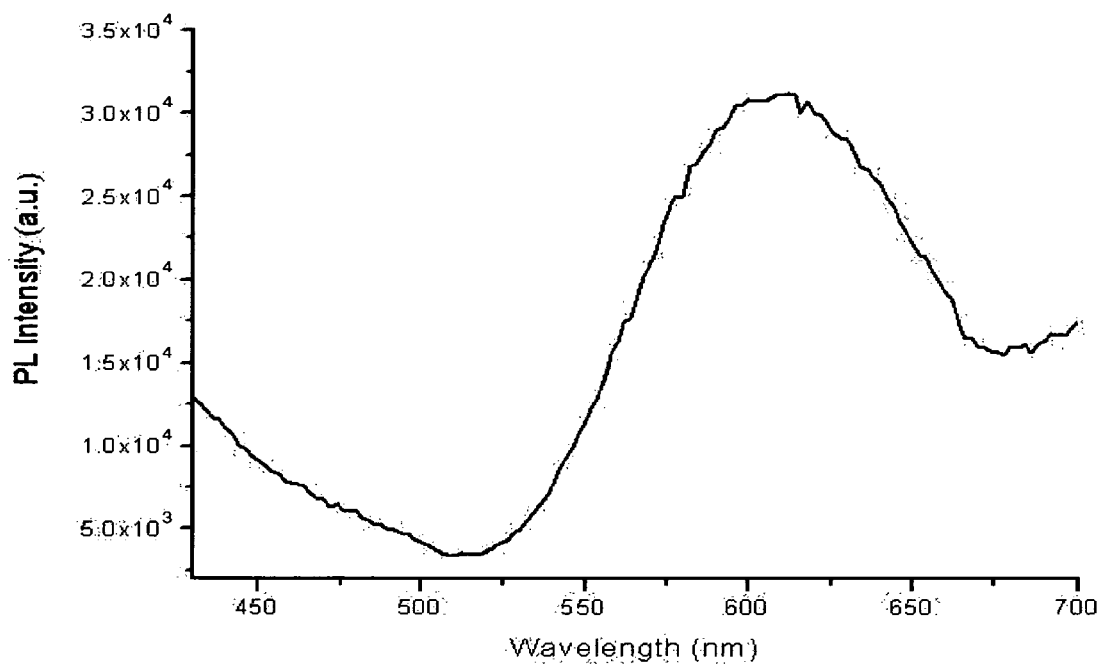
FIG. 3 is an EL spectrum of a compound of Example 3 of the present invention.

The compound in a liquid state exhibited the maximum emission intensity at the wavelength of about 613 nm, as shown in the PL spectrum of FIG. 3.

EXAMPLE 4

Synthesis of iridium (III) bis(3-dimethylamino-2-(4', 6'-difluorophenyl)pyridinato-N,C$^{2'}$)8-quinolinesulfonate (C5)

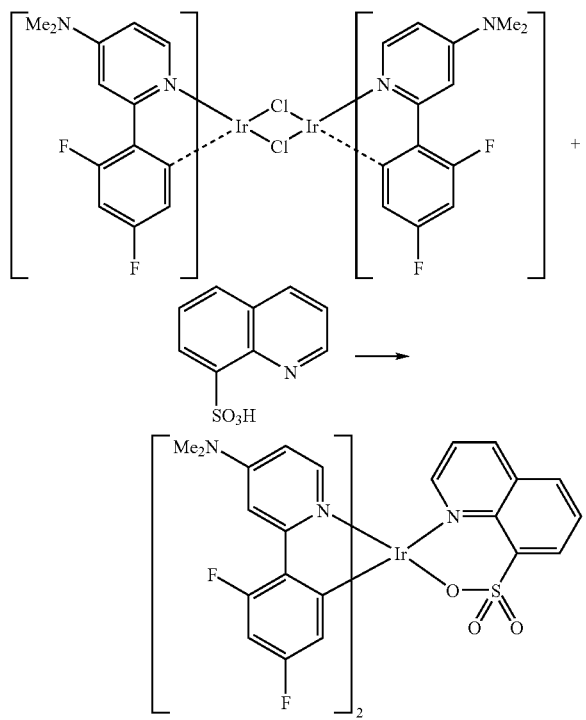

0.48 g (yield 75%) of the title compound was synthesized as a brown solid in the same manner as in Example 1 except that 0.52 g (0.37 mmol) of [(DMAFppy)$_2$IrCl]$_2$ synthesized in Reference Example 3 was used instead of 1 g (0.82 mmol) of [(F$_2$ppy)$_2$IrCl]$_2$ and 0.19 g (0.92 mmol) of 8-quinolinesulfonic acid was used instead of 0.36 g of 8-quinolinecarboxylic acid. $^1$H-NMR(CDCl$_3$): δ 3.18(s, 6H, aliphatic), 6.05 (t, 1H, aromatic), 6.25(d, 1H, aromatic), 6.43(d, 1H, aromatic), 6.62(d, 1H, aromatic), 6.75(m, 3H, aromatic), 6.98 (d, 1H, aromatic), 7.30(m, 1H, aromatic), 7.40(d, 1H, aromatic), 7.56(m, 3H, aromatic), 9.13(d, 1H, aromatic).

Figure 4:
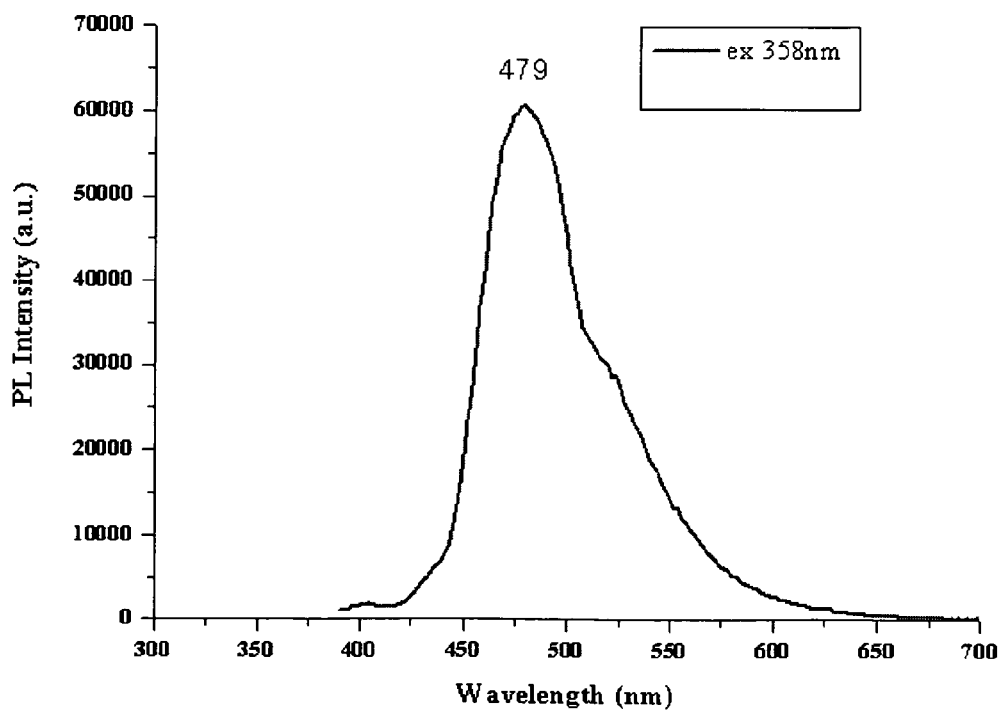
FIG. 4 is a PL spectrum of a compound of Example 4 of the present invention.

The compound exhibited the maximum emission intensity at the wavelength of 479 nm, as shown in the PL spectrum of FIG. 4.

EXAMPLE 5

Synthesis of iridium (III) bis(2-phenylpyridinato-N, C$^{2'}$)2-pyridinesulfonate (A1)

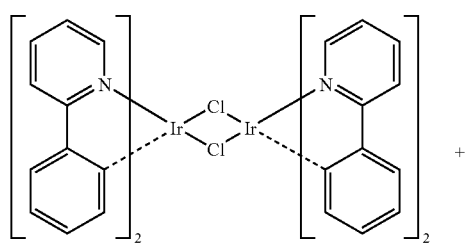

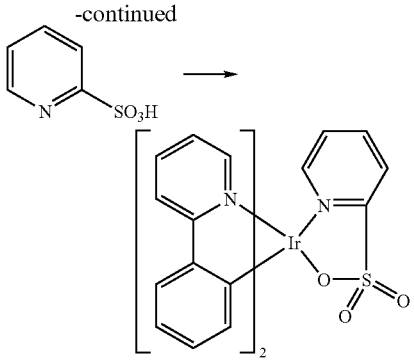

5.07 g (yield 82.62%) of the title compound was synthesized as a pure yellow solid in the same manner as in Example 1 except that 5 g (4.66 mmol) of [(ppy)$_2$IrCl]$_2$ synthesized in Reference Example 4 was used instead of 1 g (0.82 mmol) of [(F$_2$ppy)$_2$IrCl]$_2$ and 1.86 g (11.66 mmol) of 2-pyridinesulfonic acid was used instead of 0.36 g of 8-quinolinecarboxylic acid. The melting point was 395° C. or more. $^1$H-NMR(CD$_2$Cl$_2$): δ 6.11(d, 1H, aromatic), 6.30(d, 1H, aromatic), 6.77(q, 1H, aromatic), 6.92(d, 1H, aromatic), 7.06(t, 1H, aromatic), 7.59(d, 1H, aromatic), 7.65(d, 1H, aromatic), 7.75-7.93(m, 3H, aromatic), 8.11(d, 1H, aromatic), 9.12(d, 1H, aromatic).

Figure 5:
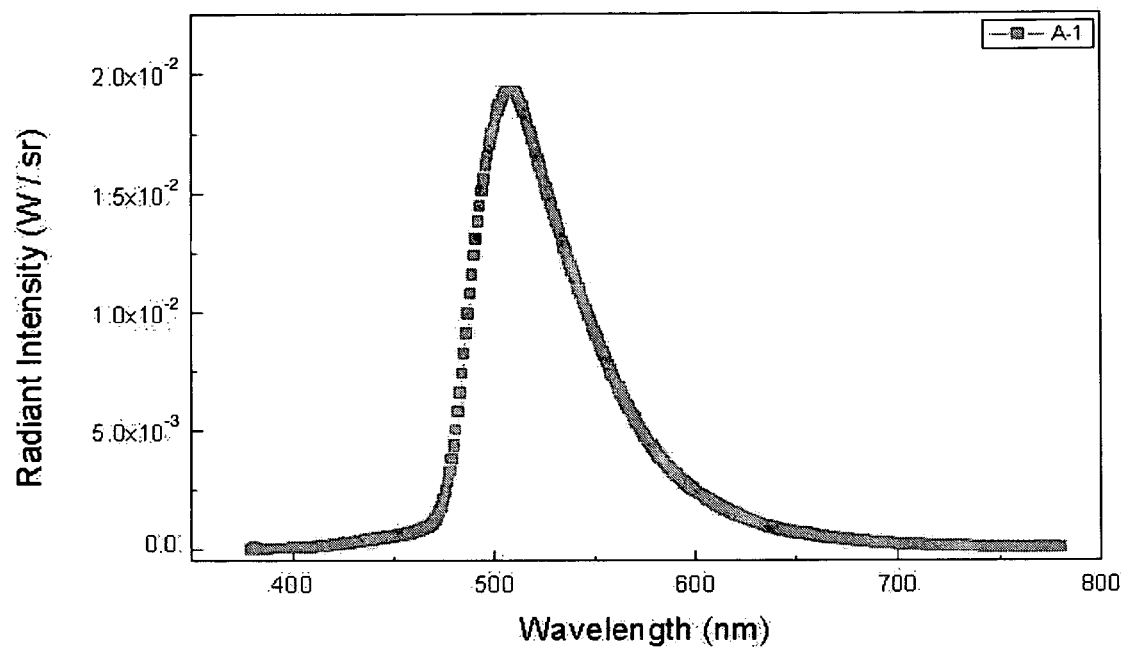
FIG. 5 is an EL spectrum of a compound of Example 5 of the present invention.

The compound exhibited the maximum emission intensity at the wavelength of 508 nm, as shown in the EL spectrum of FIG. 5.

The CIE chromaticity coordinate of the compound showed that x was 0.25 and y was 0.6.

EXAMPLE 6

Synthesis of iridium (III) bis(2-phenylpyridinato-N, C$^{2'}$)2-quinolinecarboxylate (A4)

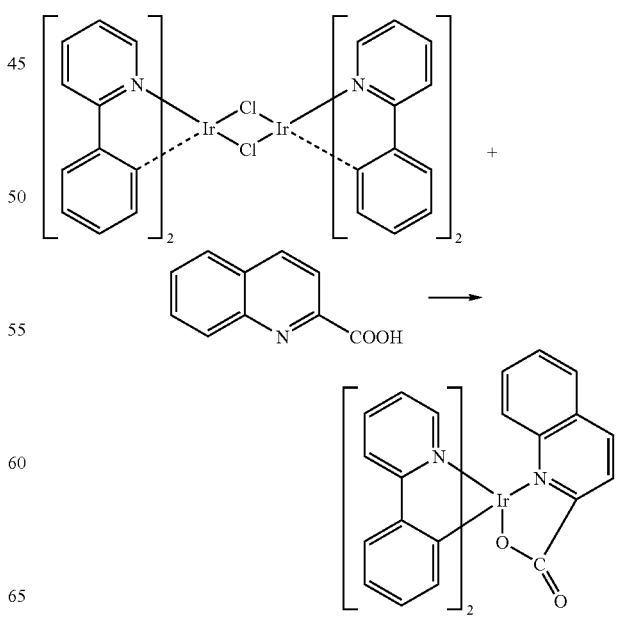

0.95 g (yield 75.81%) of the title compound was synthesized in the same manner as in Example 1 except that 1 g (0.93 mmol) of [(ppy)$_2$IrCl]$_2$ synthesized in Reference Example 4 was used instead of 1 g (0.82 mmol) of [(F$_2$ppy)$_2$IrCl]$_2$ and 0.40 g (2.33 mmol) of 2-quinolinecarboxylic acid was used instead of 0.36 g of 8-quinolinecarboxylic acid. The melting point was 375-379° C. $^1$H-NMR(CDCl$_3$): δ 6.03(d, 1H, aromatic), 6.51(d, 1H, aromatic), 6.70-6.96(m, 4H, aromatic), 7.06(t, 1H, aromatic), 7.48-7.90(m, 3H, aromatic), 8.01(d, 1H, aromatic), 8.38(d, 1H, aromatic), 8.34(d, 1H, aromatic), 8.73(d, 1H, aromatic).

Figure 6:
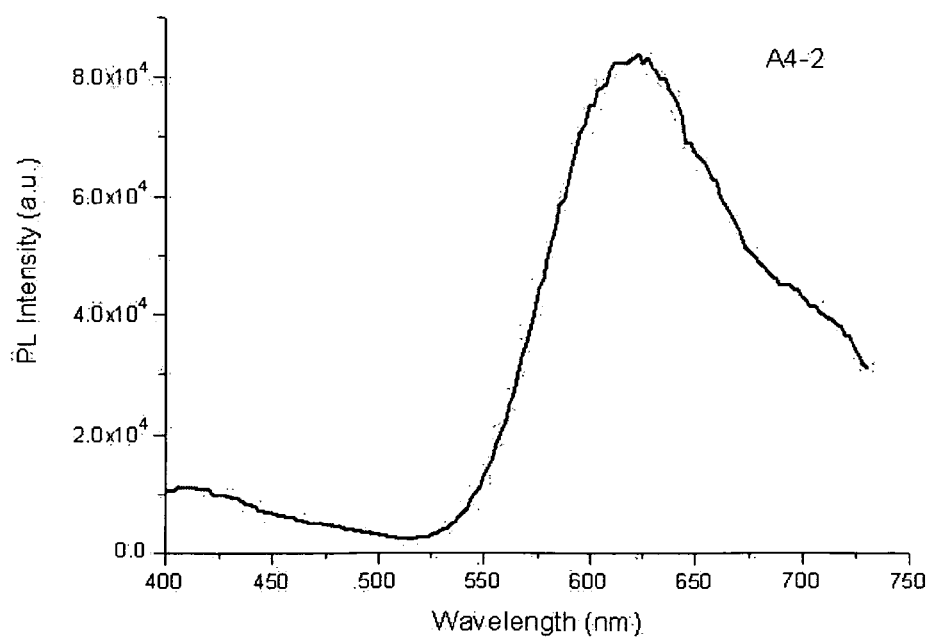
FIG. 6 is a PL spectrum of a compound of Example 6 of the present invention.

The compound exhibited the maximum emission intensity at the wavelength of about 620 nm, as shown in the PL spectrum of FIG. 6.

EXAMPLE 7

Synthesis of iridium (III) bis(2-(4',6'-difluorophenyl) pyridinato-N,C$^{2'}$)2-pyridinesulfonate (B1)

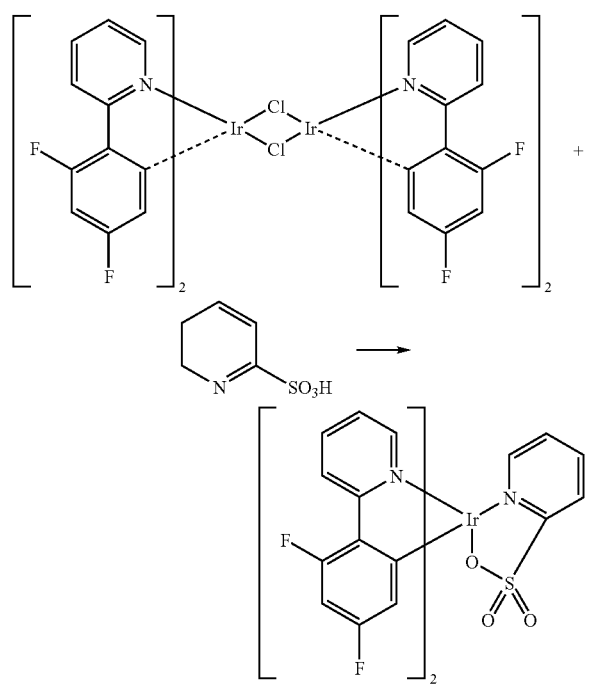

5.34 g (yield 88.93%) of the title compound was synthesized as a pure yellow solid in the same manner as in Example 1 except that 1.64 g (10.28 mmol) of 2-pyridinesulfonic acid was used instead of 0.36 g of 8-quinolinecarboxylic acid. The melting point was 345-355° C. $^1$H-NMR(CDCl$_3$): δ 5.49(d, 1H, aromatic), 5.71(d, 1H, aromatic), 6.47(m, 1H, aromatic), 7.08(t, 1H, aromatic), 7.41(t, 1H, aromatic), 7.66(d, 1H, aromatic), 8.12(d, 1H, aromatic), 8.13(d, 1H, aromatic), 8.24-8.33(m, 1H, aromatic), 9.08(d, 1H, aromatic).

Figure 7:
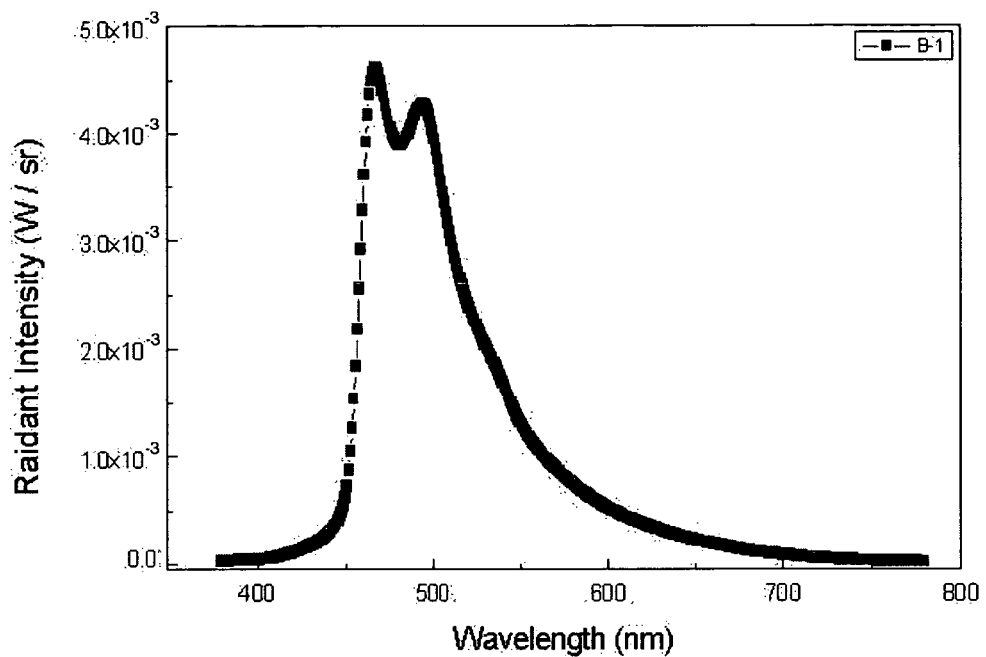
FIG. 7 is an EL spectrum of a compound of Example 7 of the present invention.

The compound in a liquid state exhibited the maximum emission intensity at the wavelength of 467 nm, as shown in the EL spectrum of FIG. 7.

The CIE chromaticity coordinate of the compound showed that x was 0.2 and y was 0.36.

EXAMPLE 8

Synthesis of iridium (III) bis(2-(4',6'-difluorophenyl) pyridinato-N,C$^{2'}$)2-quinolinecarboxylate (B4)

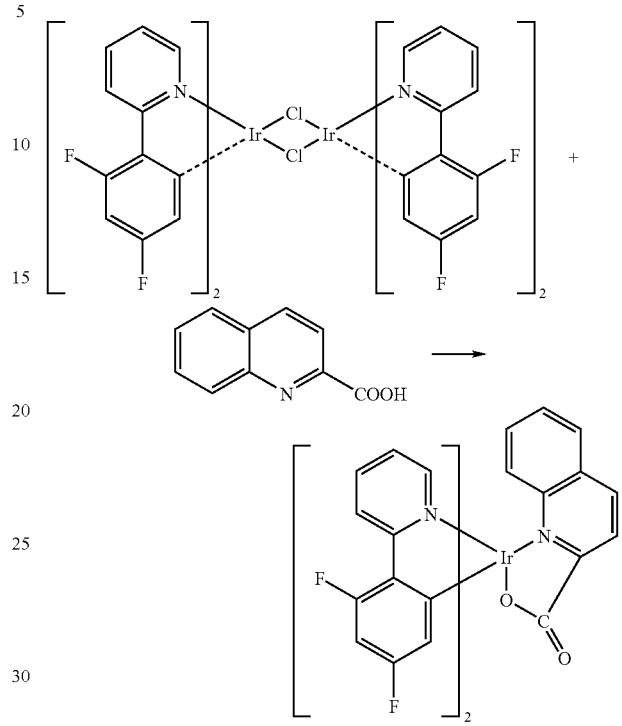

Figure 8:
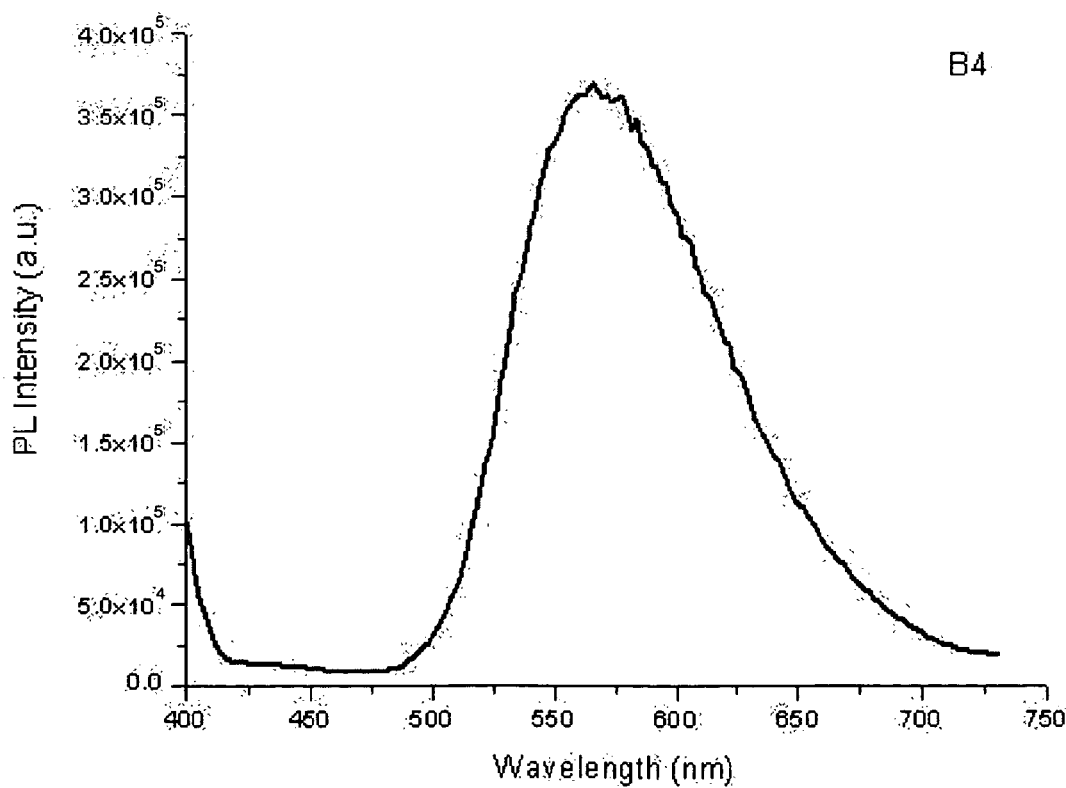
FIG. 8 is a PL spectrum of a compound of Example 8 of the present invention.

0.99 g (yield 81.10%) of the title compound was synthesized as a pure yellow solid in the same manner as in Example 1 except that 0.36 g (2.06 mmol) of 2-quinolinecarboxylic acid was used instead of 0.36 g of 8-quinolinecarboxylic acid. The melting point was 218-220° C. $^1$H-NMR(CDCl$_3$): δ 5.43 (d, 1H, aromatic), 5.94(d, 1H, aromatic), 6.45(m, 1H, aromatic), 6.85(t, 1H, aromatic), 7.12(t, 1H, aromatic), 7.38(t, 1H, aromatic), 7.72(m, 1H, aromatic), 8.18(d, 1H, aromatic), 8.32(d, 1H, aromatic), 8.43(d, 1H, aromatic), 8.54(d, 1H, aromatic), 8.67(d, 1H, aromatic):

The compound exhibited the maximum emission intensity at the wavelength of about 560 nm, as shown in the PL spectrum of FIG. 8.

EXAMPLE 9

Synthesis of iridium (III) bis(3-dimethylamino-2-(4', 6'-difluorophenyl)pyridinato-N,C$^{2'}$)2-pyridinesulfonate (C1)

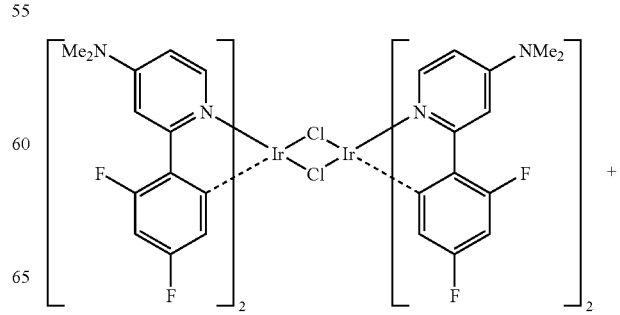

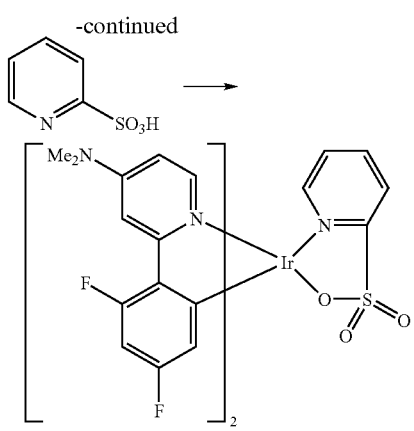

0.48 g (yield 80%) of the title compound was synthesized as a pure yellow solid in the same manner as in Example 1 except that 0.52 g (0.37 mmol) of [(DMAfppy)$_2$IrCl]$_2$ synthesized in Reference Example 3 was used instead of 1 g (0.82 mmol) of [(F$_2$ppy)$_2$IrCl]$_2$ and 0.15 g (0.92 mmol) of 2-pyridinesulfonic acid was used instead of 0.36 g of 8-quinolinecarboxylic acid. $^1$H-NMR(CDCl$_3$): δ 3.10(s, 6H, aliphatic), 5.65(d, 1H, aromatic), 5.83(d, 1H, aromatic), 6.23(d, 1H, aromatic), 6.30(m, 1H, aromatic), 6.44(d, 2H, aromatic), 7.26 (d, 1H, aromatic), 7.37(t, 1H, aromatic), 7.44(t, 1H, aromatic), 7.64(d, 1H, aromatic), 7.89(t, 1H, aromatic), 8.03(d, 1H, aromatic), 8.49(d, 1H, aromatic).

Figure 9:
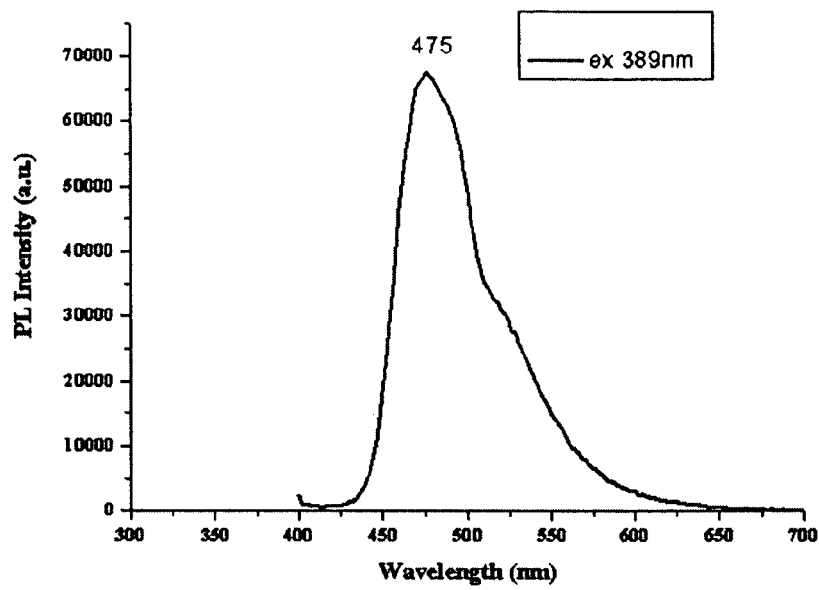
FIG. 9 is a PL spectrum of a compound of Example 9 of the present invention.

The compound in a liquid state exhibited the maximum emission intensity at the wavelength of 475 nm, as shown in the PL spectrum of FIG. 9.

EXAMPLE 10

Synthesis of iridium (III) bis(3-methyl-2-(4',6'-difluorophenyl)pyridinato-N,C$^{2'}$)2-pyridinesulfonate (D1)

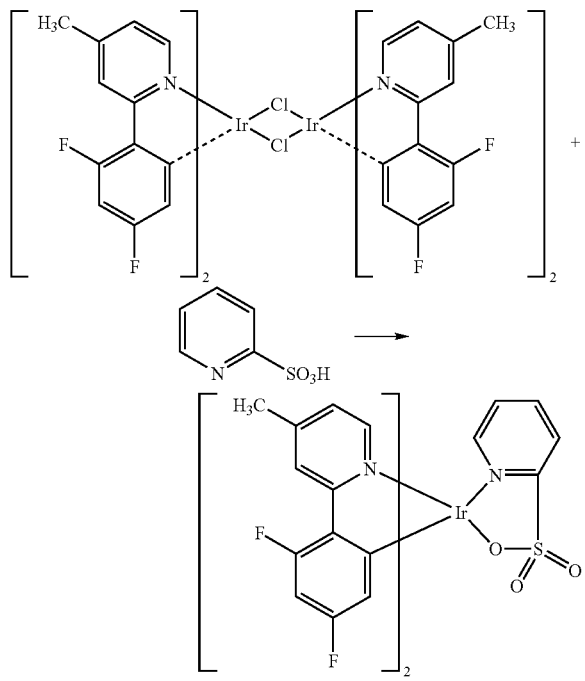

0.20 g (yield 57%) of the title compound was synthesized as a pure yellow solid in the same manner as in Example 1 except that 0.30 g (0.23 mmol) of [(Fpmp)$_2$IrCl]$_2$ synthesized in Reference Example 2 was used instead of 1 g (0.82 mmol) of [(F$_2$ppy)$_2$IrCl]$_2$ and 0.09 g (0.57 mmol) of 2-pyridinesulfonic acid was used instead of 0.36 9 of 8-quinolinecarboxylic acid. $^1$H-NMR(CDCl$_3$): δ 2.54(s, 3H, aliphatic), 5.47 (d, 1H, aromatic), 5.72(d, 1H, aromatic), 6.50(m, 2H, aromatic), 6.85(d, 1H, aromatic), 7.05(d, 1H, aromatic), 7.55 (d, 1H, aromatic), 7.62(d, 1H, aromatic), 7.96(m, 1H, aromatic), 8.02(d, 1H, aromatic), 8.08(d, 2H, aromatic), 8.85(d, 1H, aromatic).

Figure 10:
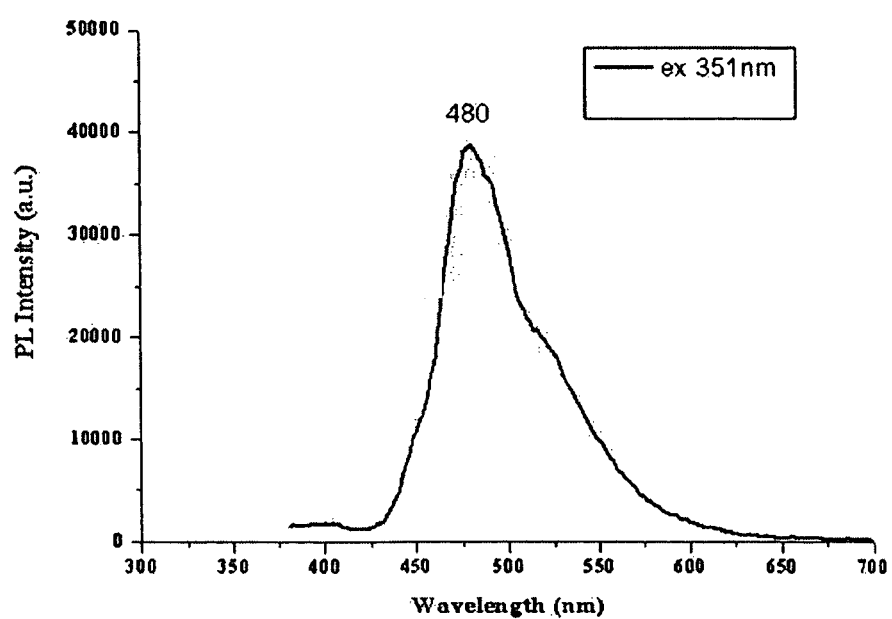
FIG. 10 is a PL spectrum of a compound of Example 10 of the present invention.

The compound in a liquid state exhibited the maximum emission intensity at the wavelength of 480 nm, as shown in the PL spectrum of FIG. 10.

As apparent from the above description, when a fused N-containing aromatic ring compound is used as an ancillary ligand, a dopant with excellent phosphorescent characteristics suitable as a blue phosphorescent material is obtained. Furthermore, incorporation of various main ligands enables realization of a full-color including red, green, and blue color.

An iridium complex of the present invention complex can efficiently emit light ranging from a blue region to a red region in a triplet MLCT state. Such an organometallic complex can be used in formation of an organic layer of an organic EL device. Furthermore, since it can be used as a high-efficiency phosphorescent material, it can produce white light emission when used together with a green-emitting material or a red-emitting material as well as emission at the wavelength range of 400-650 nm.

What is claimed is:

1. An iridium (III) complex represented by Formula 1:

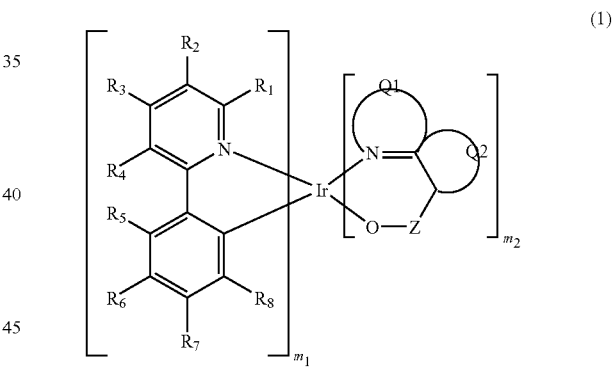

(1)

wherein Q1 is an N-containing aromatic ring, Q2 is an aromatic ring, and Q1 and Q2 form a fused ring;

Z is selected from the group consisting of a thiocarbonyl linking group (>C=S), a sulfoxide linking group (>S=O), a sulfonyl linking group (—SO$_2$—), and a combination thereof;

m$_1$ is an integer of 0 to 2 and m$_2$ is 3–m$_1$; and

R$_1$, R$_2$, R$_3$, R$_4$, R$_5$, R$_6$, R$_7$, and R$_8$ are each independently a hydrogen or a substituent.

2. The iridium (III) complex of claim 1, wherein R$_1$, R$_2$, R$_3$, R$_4$, R$_5$, R$_6$, R$_7$, and R$_8$ are each independently a substituent selected from the group consisting of an alkyl group, an alkenyl group, an alkynyl group, an aryl group, an amino group, an alkoxy group, an aryloxy group, a heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclic thio group, a sulfonyl group, a sulfinyl group, an ureido group, a phosphoramide group, a hydroxy group, a mercapto group, a halogen atom, a cyano group, a sulfo group, a carboxyl group, a nitro group, a hydroxaminic group, a sulfino group, a hydrazino group, an imino group, a heterocyclic group, a silyl group, and a silyloxy group.

3. The iridium (III) complex of claim 1, wherein the fused ring formed by Q1 and Q2 is derived from one selected from the group consisting of indole, azaindole, carbazole, indazole, harmane, benzimidazole, benzotriazole, benzoxazole, benzothiazole, benzoselenadiazole, benzothiadiazole, benzisoxazole, quinoline, benzoquinoline, acridine, isoquinoline, and a derivative thereof.

4. The iridium (III) complex of claim 1, wherein the compound of the formula 1 is a compound represented by Formula 3:

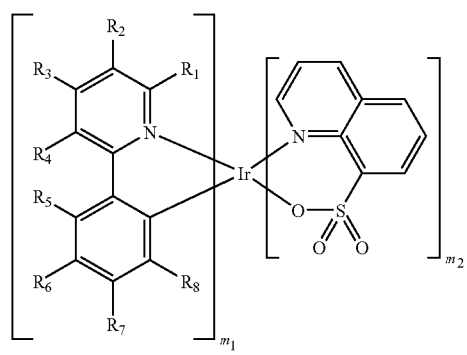

(3)

wherein $R_1$, $R_2$, $R_3$, $R_4$, $R_5$, $R_6$, $R_7$, $R_8$ are each independently a hydrogen or a substituent, $m_1$ is an integer of 0 to 2, and $m_2$ is $3-m_1$.

5. The iridium (III) complex of claim 1, wherein the iridium (III) complex is selected from the group consisting of compounds represented by the following formulae:

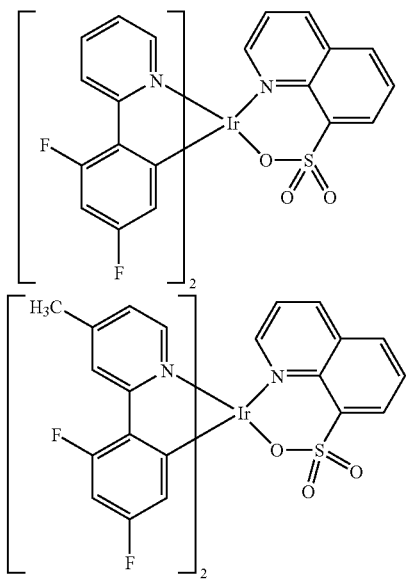

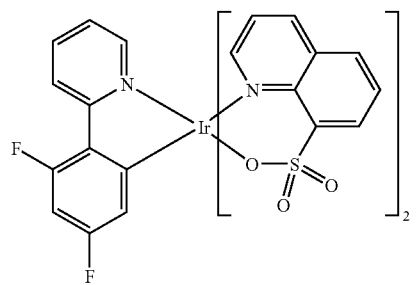

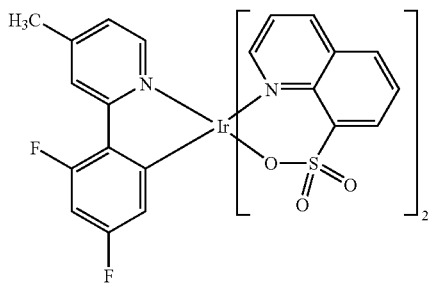

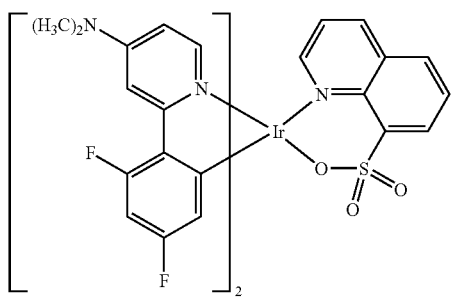

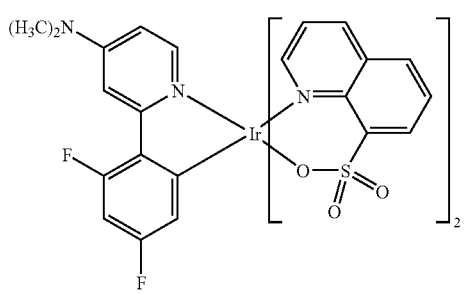

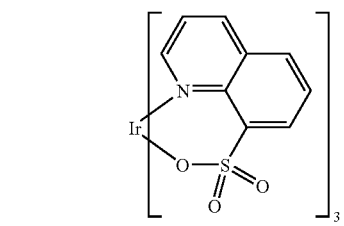

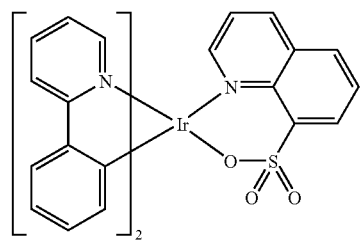

-continued

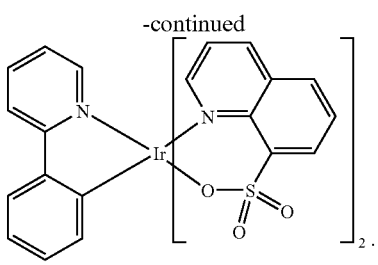

6. An organic electroluminescent device, comprising:
a pair of electrodes; and
an organic layer interposed between the pair of electrodes, the organic layer comprising an iridium (III) complex represented by Formula 1:

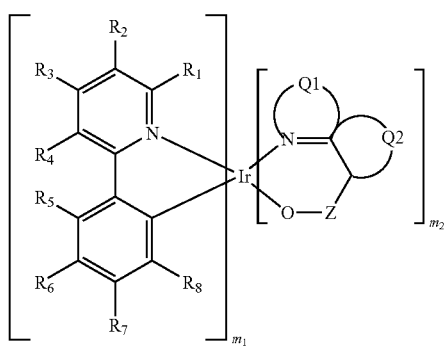

(1)

wherein Q1 is an N-containing aromatic ring, Q2 is an aromatic ring, and Q1 and Q2 form a fused ring;
Z is selected from the group consisting of a thiocarbonyl linking group (>C=S), a sulfoxide linking group (>S=O), a sulfonyl linking group (—SO$_2$—), and a combination thereof;
$m_1$ is an integer of 0 to 2 and $m_2$ is 3−$m_1$; and
$R_1$, $R_2$, $R_3$, $R_4$, $R_5$, $R_6$, $R_7$, and $R_8$ are each independently a hydrogen or a substituent.

7. The organic electroluminescent device of claim 6, wherein the organic layer further comprises at least one selected from the group consisting of at least one polymeric host, a mixture of a polymeric host and a small molecular host, a small molecular host, and a non-emission polymeric matrix.

8. The organic electroluminescent device of claim 6, wherein the organic layer comprises a light emission layer comprising 1 to 30 parts by weight of the iridium complex, based on 100 parts by weight of the total weight of the light emission layer.

9. The organic electroluminescent device of claim 6, wherein the organic layer further comprises a green-emitting material or a red-emitting material.

10. The organic electroluminescent device of claim 6, wherein the thickness of the organic layer ranges from 30 to 100 nm.

11. The organic electroluminescent device of claim 6, wherein $R_1$, $R_2$, $R_3$, $R_4$, $R_5$, $R_6$, $R_7$, and $R_8$ are each independently a substituent selected from the group consisting of an alkyl group, an alkenyl group, an alkynyl group, an aryl group, an amino group, an alkoxy group, an aryloxy group, a heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclic thio group, a sulfonyl group, a sulfinyl group, an ureido group, a phosphoramide group, a hydroxy group, a mercapto group, a halogen atom, a cyano group, a sulfo group, a carboxyl group, a nitro group, a hydroxaminic group, a sulfino group, a hydrazino group, an imino group, a heterocyclic group, a silyl group, and a silyloxy group.

12. The organic electroluminescent device of claim 6, wherein the fused ring formed by Q1 and Q2 is derived from one selected from the group consisting of indole, azaindole, carbazole, indazole, harmane, benzimidazole, benzotriazole, benzoxazole, benzothiazole, benzoselenadiazole, benzothiadiazole, benzisoxazole, quinoline, benzoquinoline, acridine, isoquinoline, and a derivative thereof.

13. The organic electroluminescent device of claim 6, wherein the iridium (III) complex is represented by Formula 3:

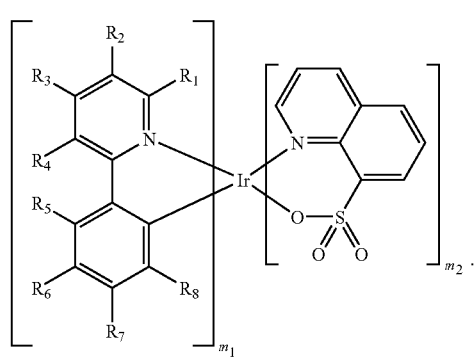

(3)

14. The organic electroluminescent device of claim 6, wherein the iridium (III) complex is selected from the group consisting of compounds represented by the following formulae:

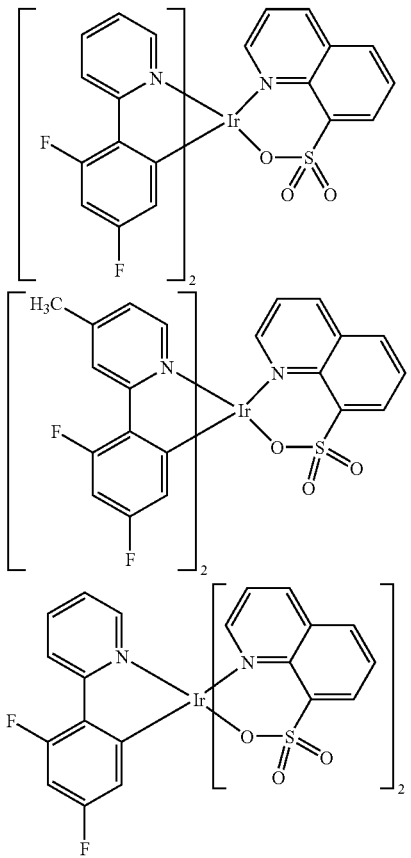

-continued
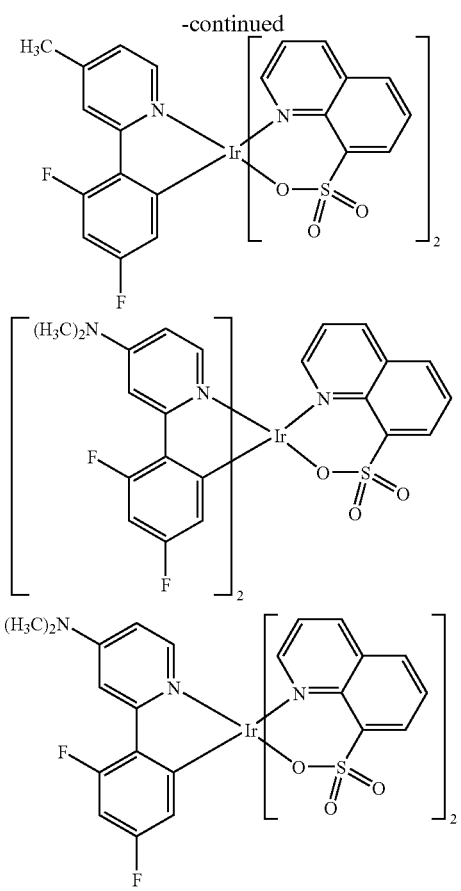
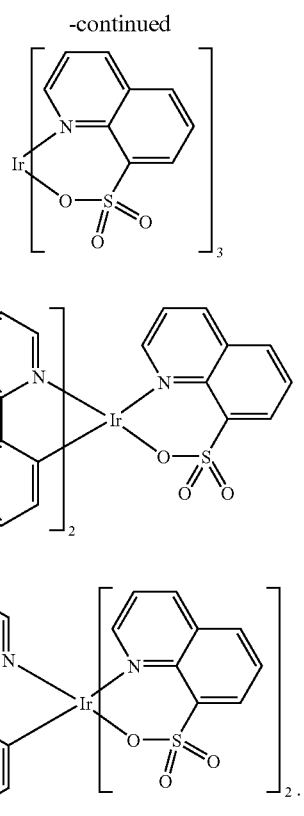
* * * * *